United States Patent [19]

Petersen et al.

[11] Patent Number: 5,480,879
[45] Date of Patent: Jan. 2, 1996

[54] QUINOLONECARBOXYLIC ACIDS

[75] Inventors: Uwe Petersen, Leverkusen; Wilfried Schröck; Dieter Häbich, both of Wuppertal; Andreas Krebs, Odenthal; Thomas Schenke, Bergisch Gladbach; Thomas Philipps, Cologne; Klaus Grohe, Odenthal; Rainer Endermann, Wuppertal; Klaus-Dieter Bremm, Wuppertal; Karl-Georg Metzger, Wuppertal, all of Germany

[73] Assignee: Bayer Aktiengesellschaft, Leverkusen, Germany

[21] Appl. No.: 131,253

[22] Filed: Oct. 1, 1993

[30] Foreign Application Priority Data

Oct. 9, 1992 [DE] Germany ............ 42 34 078.0

[51] Int. Cl.⁶ .................. C07D 487/04; A61K 31/545
[52] U.S. Cl. .................. 514/202; 514/206; 540/222; 540/225
[58] Field of Search .................. 540/222, 221, 540/226; 514/206, 202

[56] References Cited

U.S. PATENT DOCUMENTS 4,990,517  2/1991  Petersen et al. .
5,059,597  10/1991 Petersen et al. .
5,329,002  7/1994  Albrecht et al. ............ 540/222

FOREIGN PATENT DOCUMENTS

| 0335297 | 10/1989 | European Pat. Off. . |
| 0350733 | of 1990 | European Pat. Off. . |
| 0366189 | 5/1990 | European Pat. Off. . |
| 0391132 | 10/1990 | European Pat. Off. . |
| 0451764 | 10/1991 | European Pat. Off. . |
| 0492277 | 7/1992 | European Pat. Off. . |

OTHER PUBLICATIONS

Chemical Abstracts vol. 121:230582 (1984).
V. G. Blaschke, "Chromatographische Racemattrennung", Angew. Chem 92, 14–25, (1980).
T. W. Greene, *Protective Groups in Organic Synthesis*, John Wiley & Sons, (1984), Title page and Table of Contents (ix–x).
J. F. W. McOmie, "protective Groups in Org. Chemistry" (1973), p. 43.
Chemical Abstracts, vol. 116, Jan. 20, 1992, No. 3.

*Primary Examiner*—Nicholas Rizzo
*Attorney, Agent, or Firm*—Sprung Horn Kramer & Woods

[57] ABSTRACT

The invention relates to novel derivatives of quinolonecarboxylic acid and naphthyridonecarboxylic acid which are linked to a β-lactam antibiotic, to their salts, to processes for their preparation and to antibacterial agents containing these derivatives.

9 Claims, No Drawings

QUINOLONECARBOXYLIC ACIDS

The invention relates to novel derivatives of quinolonecarboxylic acid and naphthyridonecarboxylic acid which are linked to a β-lactam antibiotic, to their salts, to processes for their preparation and to antibacterial agents containing these derivatives.

Compounds in which a quinolone is linked to a cephalosporin have already become known from the European Patent Applications 0 335 297 and 0 492 277. However, the compounds exhibit too low an activity towards Gram-positive bacteria.

Compounds of the formula (I) have been found

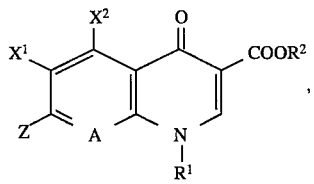
(I)

in which
$X^1$ represents halogen,
$X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl,
$R^1$ represents alkyl having 1 to 4 carbon atoms, alkenyl having 2 to 4 carbon atoms, cycloalkyl having 3 to 6 carbon atoms, bicyclo[1.1.1]pent-1-yl, 1,1-dimethylpropargyl, 3-oxetanyl, 2-hydroxyethyl, 2-fluoroethyl, methoxy, amino, methylamino, ethylamino, dimethylamino, or phenyl which is optionally substituted by 1 or 2 fluorine atoms,
$R^2$ represents hydrogen, alkyl having 1 to 5 carbon atoms, which is optionally substituted by hydroxyl, methoxy, amino, methylamino or dimethylamino, or (5-methyl-2-oxo-1,3-dioxol-4-yl)-methyl,
A represents N or C—$R^5$, in which
$R^5$ represents hydrogen, halogen, methyl, alkenyl having 2 to 3 carbon atoms, alkinyl having 2 to 3 carbon atoms, hydroxyl or methoxy, or can, together with $R^1$, form a bridge of the structure

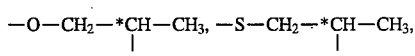

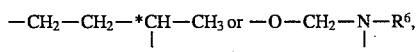

in which $R^6$ denotes hydrogen, methyl or formyl, and
Z represents a residue of the structure

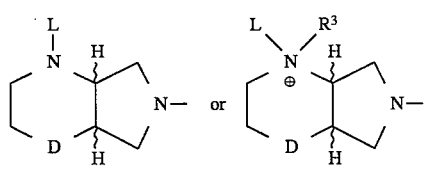

in which
D represents $CH_2$ or O,
$R^3$ represents methyl or ethyl and

L represents a residue of the structure

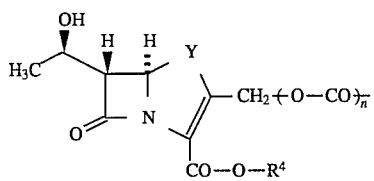

or

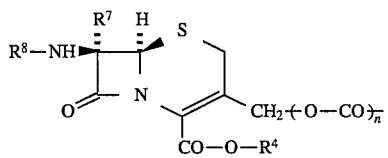

in which
n represents 0 or 1,
Y represents $CH_2$, CH—$CH_3$ or S,
$R^4$ represents H, benzyl, 4-methoxybenzyl, benzhydryl, allyl, (5-methyl-2-oxo-1,3-dioxol-4-yl)-methyl or a radical

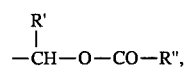

in which
R' denotes H or methyl and
R" denotes ethoxy or tert-butyl,
$R^7$ represents H or methoxy and
$R^8$ represents H, tri-($C_1$–$C_4$-alkyl)-silyl, acyl, $C_1$–$C_4$-alkoxycarbonyl, benzyloxycarbonyl, allyloxycarbonyl or isopropenyloxycarbonyl, as have their pharmaceutically utilisable hydrates and acid-addition salts, as well as the alkali metal, alkaline earth metal, silver and guanidinium salts of the underlying carboxylic acids. They exhibit a strong antibacterial effect, in particular towards Gram-positive bacteria.

The compounds which are preferred are those of the formula (I) in which
$X^1$ represents fluorine,
$X^2$ represents hydrogen, amino, methylamino, hydroxyl, methoxy, fluorine, chlorine, bromine or methyl,
$R^1$ represents alkyl having 1 to 3 carbon atoms, vinyl, cycloalkyl having 3 to 4 carbon atoms, or phenyl which is optionally substituted by 1 or 2 fluorine atoms,
$R^2$ represents hydrogen, alkyl having 1 to 2 carbon atoms, which is optionally substituted by amino, methylamino or dimethylamino, or (5-methyl-2-oxo-1,3-dioxol-4-yl)-methyl,
A represents N or C—$R^5$, in which
$R^5$ represents hydrogen, fluorine, chlorine, methyl, vinyl, ethinyl or methoxy, or can, together with $R^1$, form a bridge of the structure

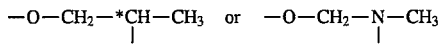

and

Z represents a residue of the structure

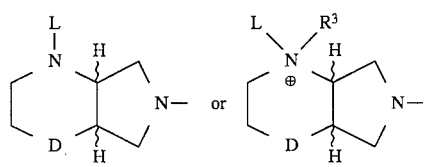

in which
D represents $CH_2$ or O,
$R^3$ represents methyl and
L represents a residue of the structure

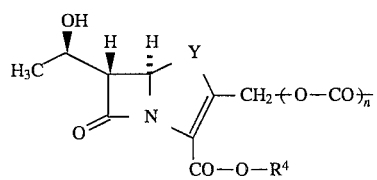

or

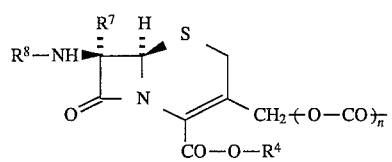

in which
n represents 0 or 1,
Y represents $CH_2$ or S,
$R^4$ represents H, benzhydryl, allyl, or a radical

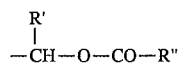

in which
R' denotes H or methyl and
R" denotes tert-butyl,
$R^7$ represents H and
$R^8$ represents H, $(CH_3)_3Si—$,

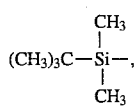

tert-butoxycarbonyl, benzyloxycarbonyl, allyloxycarbonyl, isopropenyloxycarbonyl,

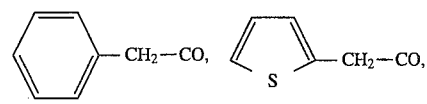

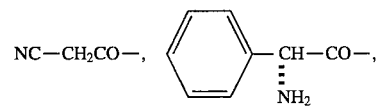

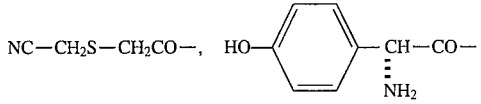

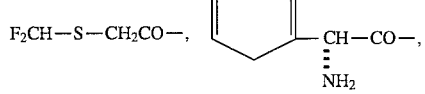

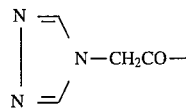

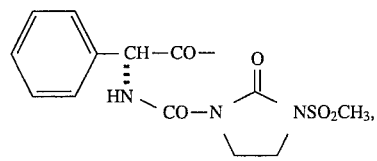

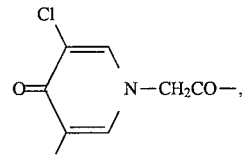

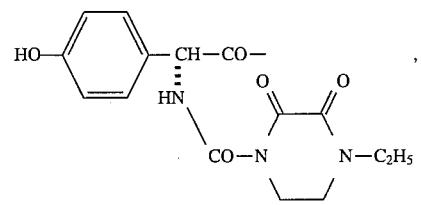

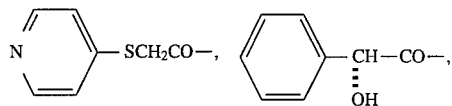

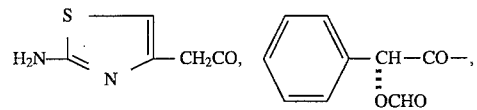

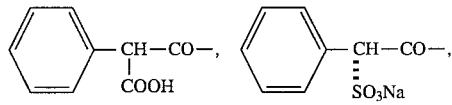

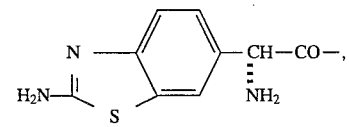

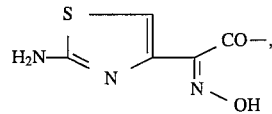

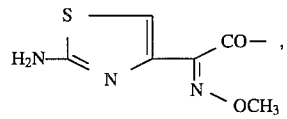

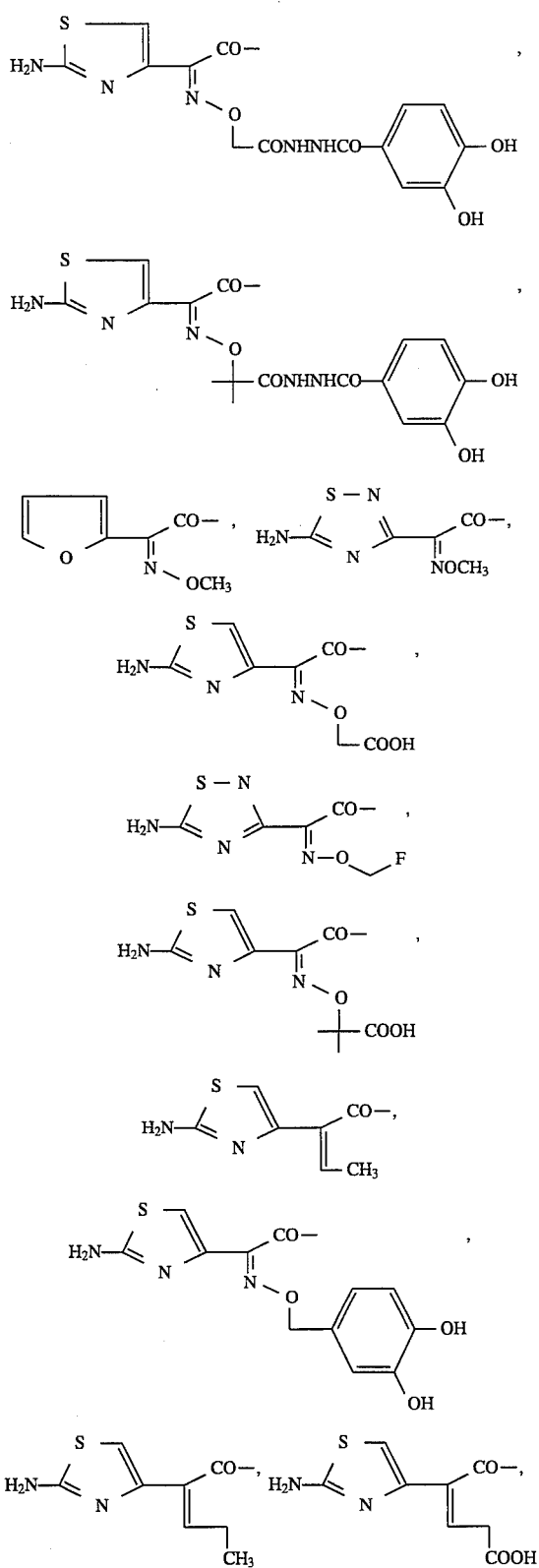

and their pharmaceutically utilisable hydrates and acid-addition salts, as well as the alkali metal, alkaline earth metal, silver and guanidinium salts of the underlying carboxylic acids.

The compounds which are particularly preferred are those of the formula (I) in which $X^1$ represents fluorine, $X^2$ represents hydrogen, amino or fluorine, $R^1$ represents alkyl having 1 to 2 carbon atoms, cyclopropyl, or phenyl which is optionally substituted by 1 or 2 fluorine atoms, $R^2$ represents hydrogen or alkyl having 1 to 2 carbon atoms, A represents N or C—$R^5$, in which $R^5$ represents hydrogen, fluorine, chlorine or methoxy, or can, together with $R^1$, form a bridge of the structure

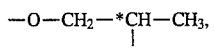

Z represents a residue of the structure

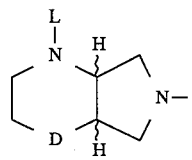

in which

D represents $CH_2$ or O,

L represents a residue of the structure

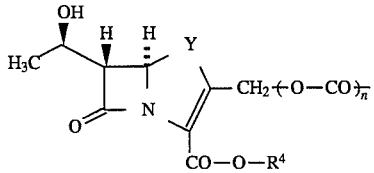

or

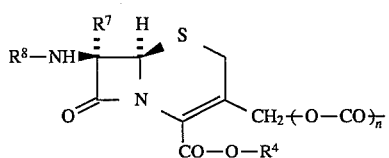

in which n represents 0 or 1,

Y represents S, $R^4$ represents H, benzhydryl or allyl, $R^7$ represents H and $R^8$ represents H, $(CH_3)_3Si$—,

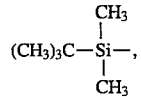

tertbutoxycarbonyl, allyloxycarbonyl,

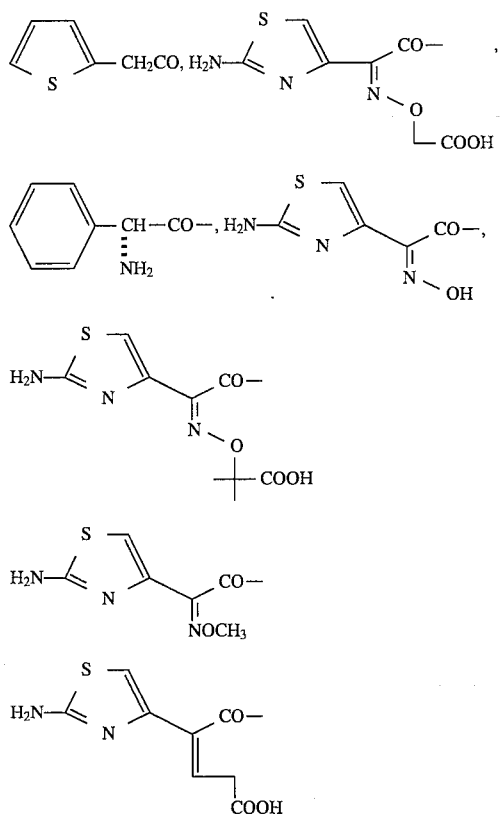

and their pharmaceutically utilisable hydrates and acid-addition salts, as well as the alkali metal, alkaline earth metal, silver and guanidinium salts of the underlying carboxylic acids.

It has furthermore been found that the compounds of the formula (I) are obtained if a compound of the formula (II)

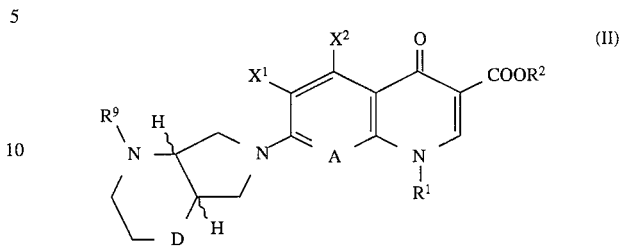

in which

A, $R^1$, $R^2$, $X^1$, $X^2$ and D have the abovementioned meaning, and $R^9$ represents H, $CH_3$ or $C_2H_5$, is reacted with compounds of the formula (III)

$$L—X^3 \qquad (III)$$

in which

L has the abovementioned meaning and $X^3$ represents halogen, in particular chlorine, bromine or iodine, or acetoxy, optionally in the presence of acid-capturing agents, and protective groups which may be present are eliminated.

If, for example, 8-chloro-1-cyclopropyl-7-([S,S]-2,8-di-azabicyclo[4.3.0]non-8-yl)-6-fluoro-1,4-dihydro-4-oxo-3-quinolinecarboxylic acid (2) and benzhydryl (6R,7R) 3-chloromethyl- 8-oxo-7-phenylacetylamino-5-thia-1-azabicyclo[4.2.0]oct-2-ene-2-carboxylate (1) are used as the starting compounds, the course of the reaction can then be represented by the following formula scheme:

Scheme 1:

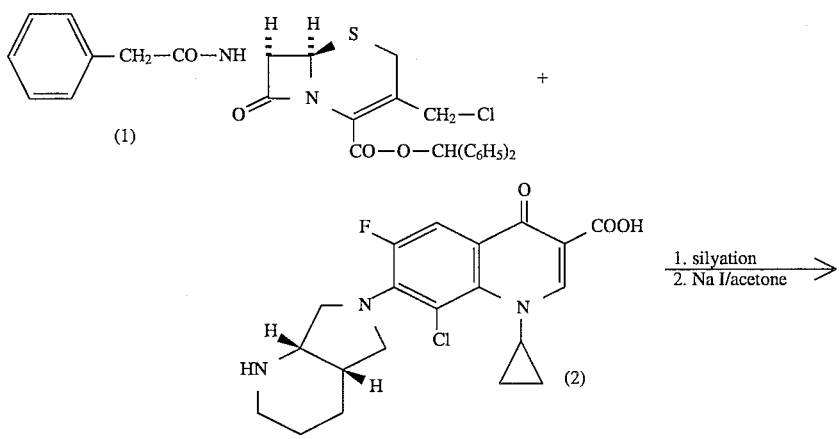

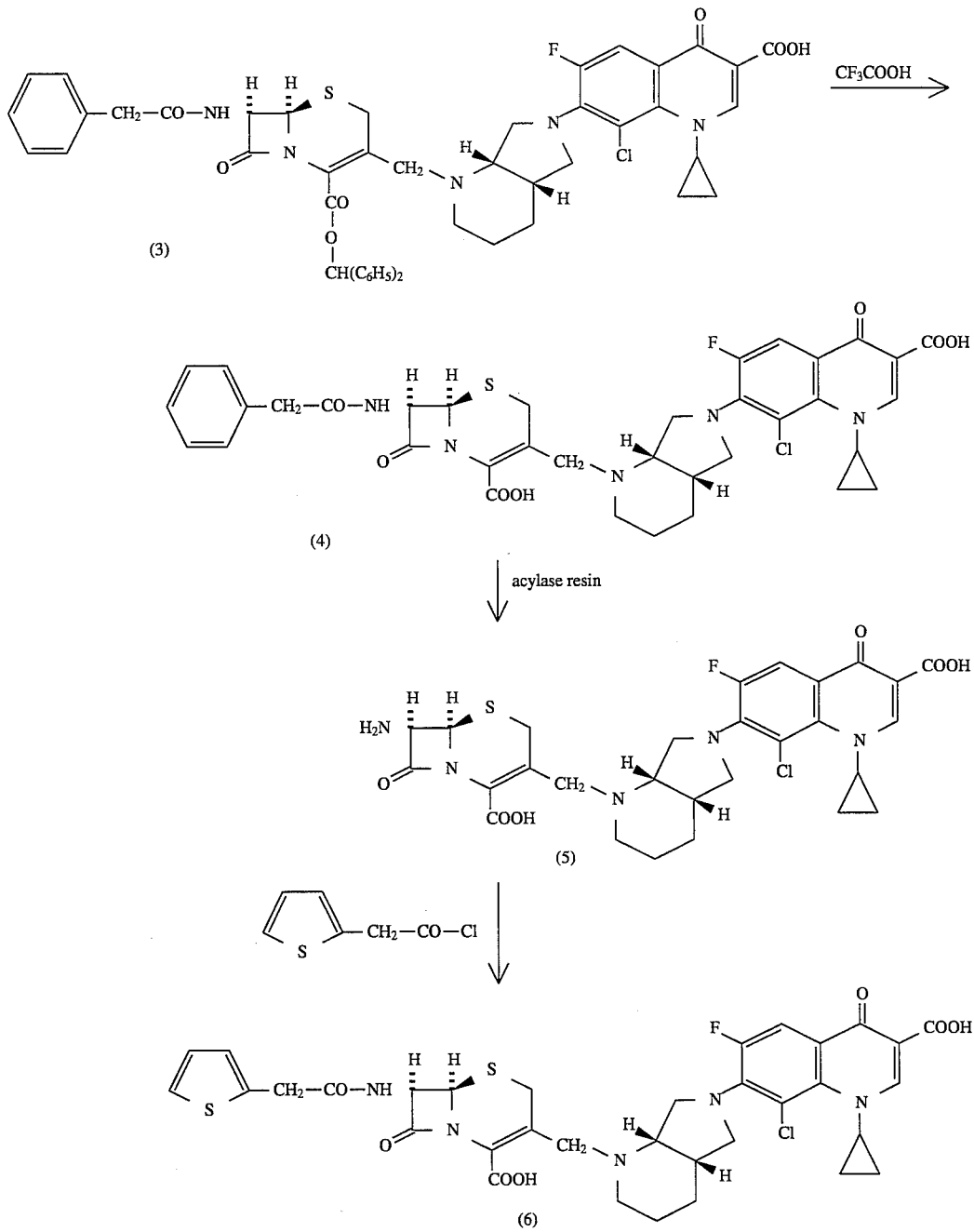

The active compound of the type of the formula (4) can, for example, be deacylated with an acylase to give the compound (5). This 7-aminocephalosporanic acid (5) is a suitable starting compound for linking to different acyl residues to give new active compounds of the type (6) in which the quinolone moiety can also be replaced by other quinolone residues of the present invention.

If, for example, allyl 6-(1-tert-butyl-dimethyl-silyloxy-ethyl)- 3-hydroxymethyl-7-oxo-4-thia-1-aza-bicyclo[3.2.0] hept- 2-ene-2-carboxylate (7) and the quinolonecarboxylic acid (2) are used as the starting compounds, the course of the reaction can then be represented by the following formula scheme:

Scheme 2:
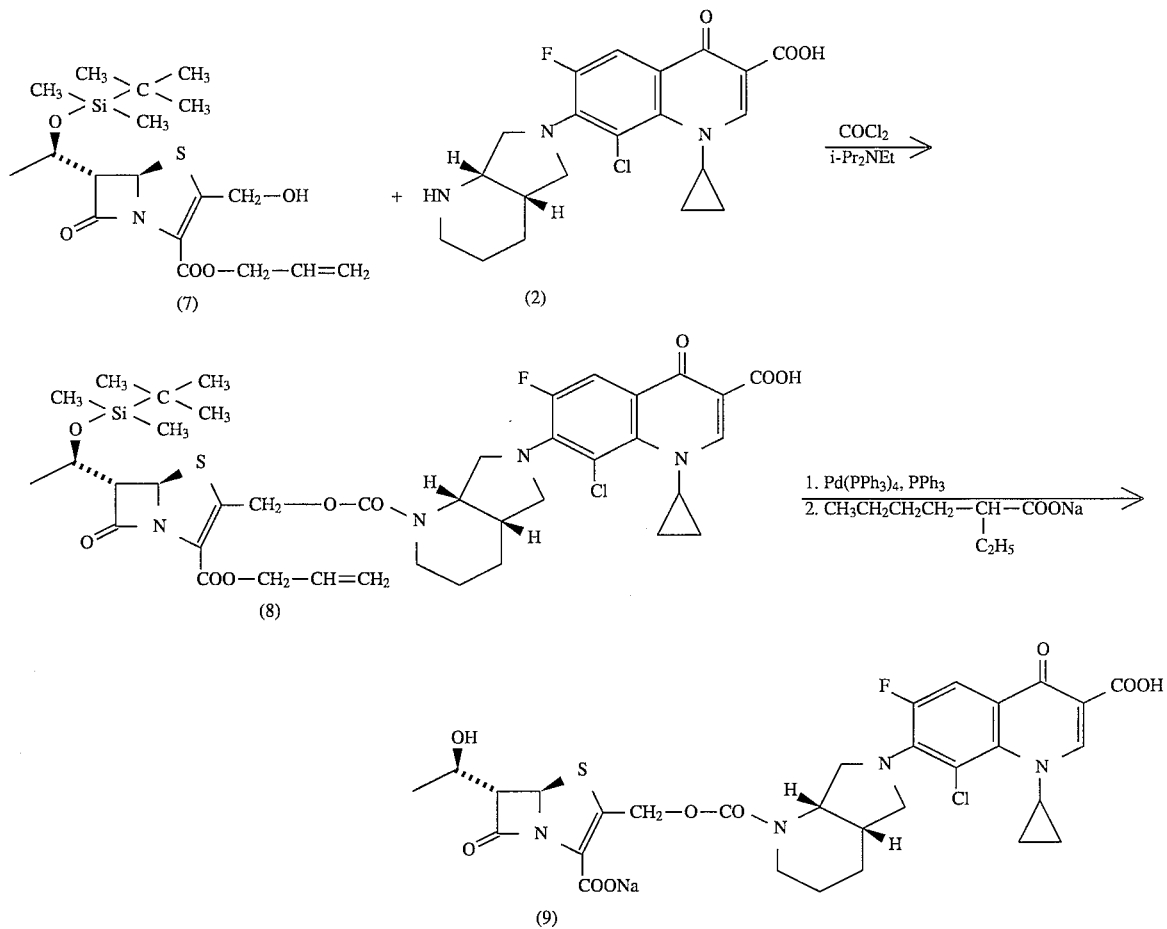
If, for example, 3-acetoxymethyl-7-[2-(2-tritylaminothiazol- 4-yl)-2-methoxyimino-acetylamino]-8-oxo-5-thia-1-aza-bicyclo[ 4.2.0]oct-2-ene-2-carboxylic acid (10) and the quinolonecarboxylic acid (2) are used as the starting compounds, the course of the reaction can then be represented by the following formula scheme:
Scheme 3:
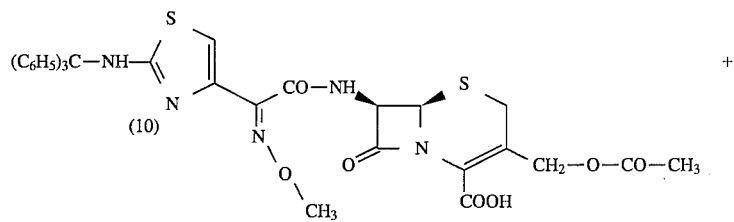

Scheme 3:
-continued
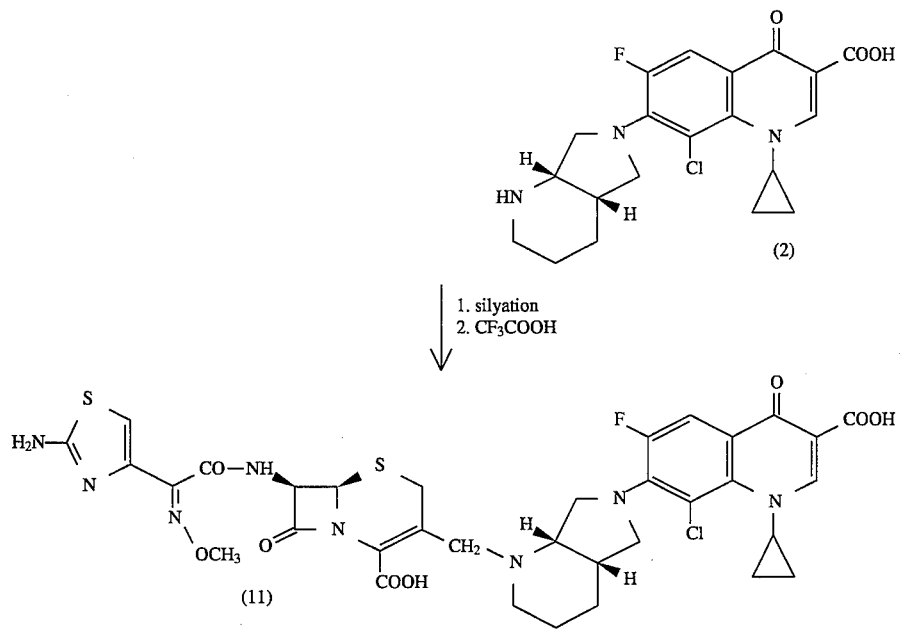
Benzhydryl 7-amino-3-chloromethyl-8-oxo-5-thia-1-azabicyclo[4.2.0]oct-2-ene-2-carboxylate (12) can, for example, also be used as starting compound and, after acylation with an activated carboxylic acid derivative to give (13), can, for example, be reacted with the quinolinecarboxylic acid (2) to give (14). After elimination of the ester protective groups, (15) is obtained:
Scheme 4:
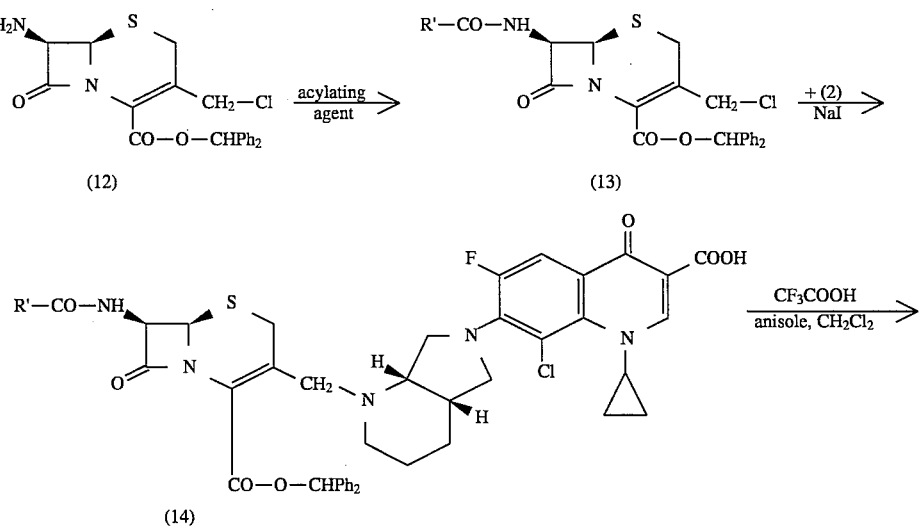

Scheme 4:
-continued

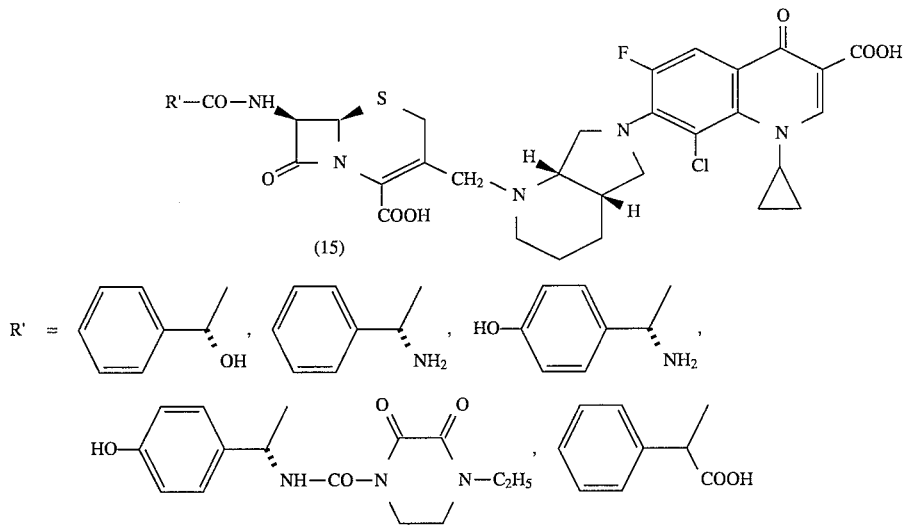

(15)

R' = [structures shown]

If the compound (12) is reacted with S-(benzothiazol-2-yl) 2-(2-amino-thiazol-4-yl)-2-oxo-thioacetate (16) according to the reaction sequence indicated in Scheme 4, a reaction product (17) is then obtained which can be condensed with hydroxylamine derivatives (18) to give the active compounds (19):

The linking of a carbapenem to the quinolone can, for example, also take place according to the following formula scheme:

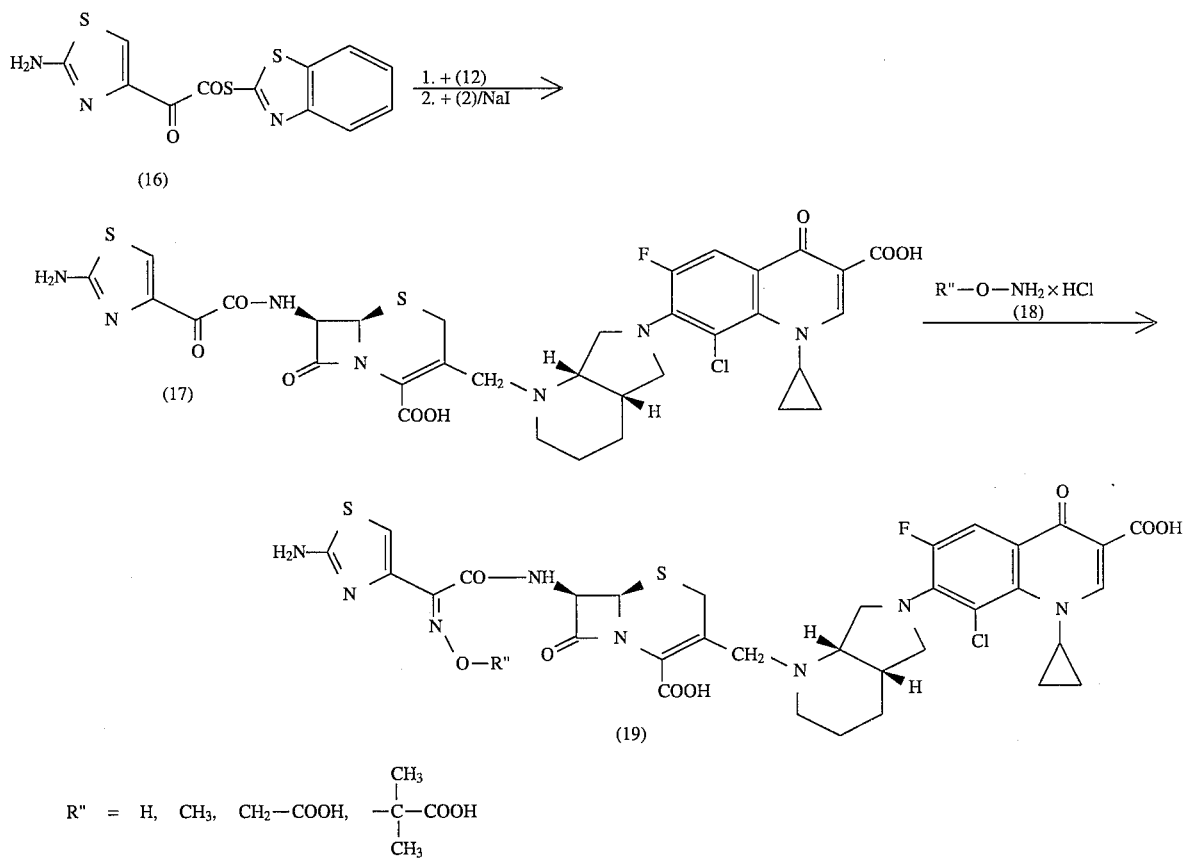

R" = H, CH$_3$, CH$_2$—COOH, $-\underset{\underset{CH_3}{|}}{\overset{\overset{CH_3}{|}}{C}}$—COOH

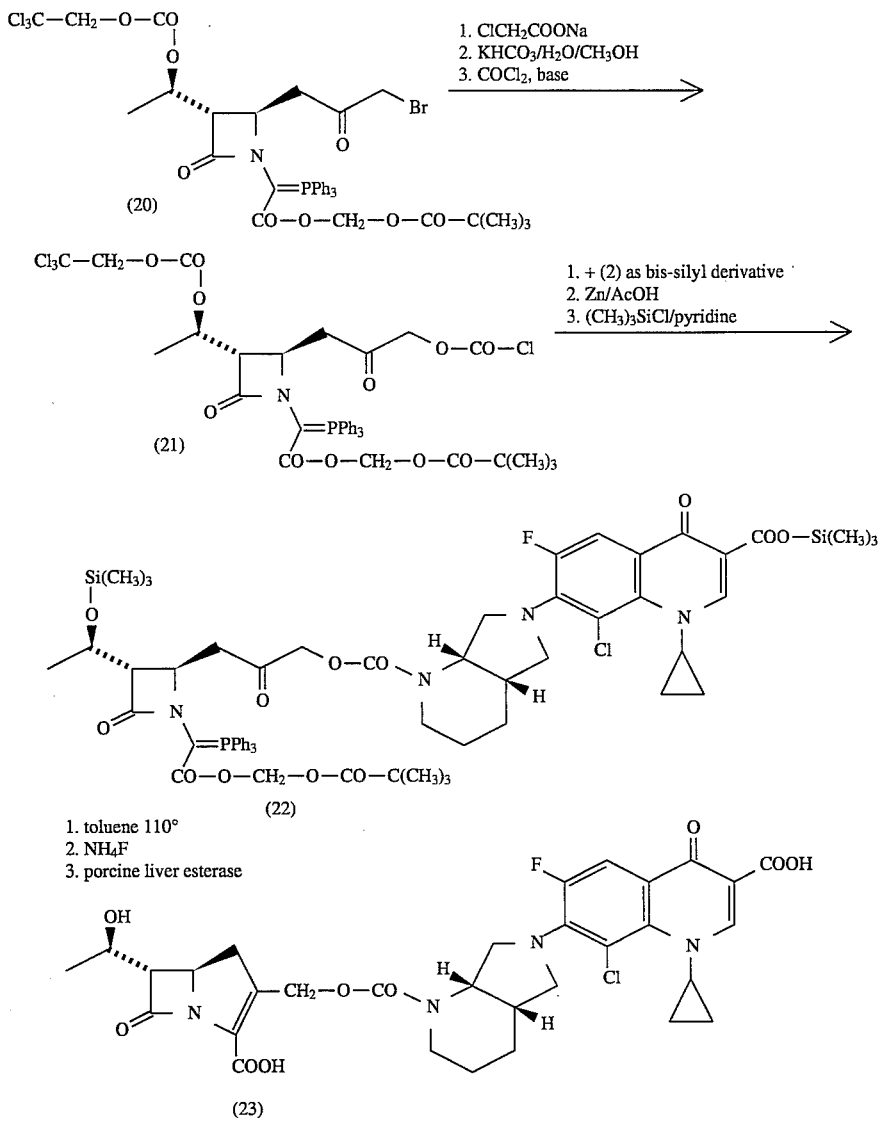

The starting compounds of the formula (I) are known in part, as racemic compounds, from EP-A-0 350 733. Enantiomerically pure starting compounds of the formula (II) are novel.

To prepare enantomerically pure intermediates of the formula (II), a compound of the formula (IV)

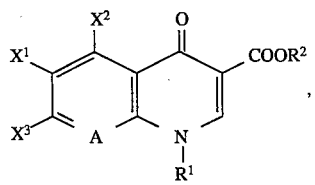

in which

A, $R^1$, $R^2$, $X^1$ and $X^2$ have the abovementioned meaning and $X^3$ represents halogen, in particular fluorine or chlorine, is reacted with enantiomerically pure compounds of the formula (V)

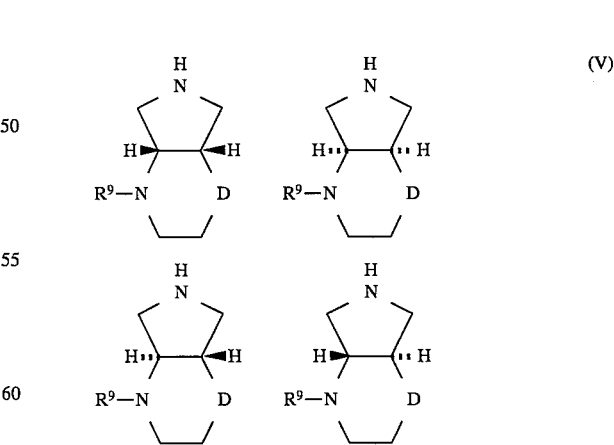

in which

D represents O or $CH_2$ and $R^9$ represents H, $CH_3$ or $C_2H_5$, optionally in the presence of acid-capturing agents.

If, for example, 8-chloro-1-cyclopropyl-6,7-difluoro-1,4-dihydro- 4-oxo-3-quinolinecarboxylic acid and [S,S]-2,8-diazabicyclo[ 4.3.0]nonane are used as the starting compounds, the course of the reaction can then be represented by the following formula scheme:

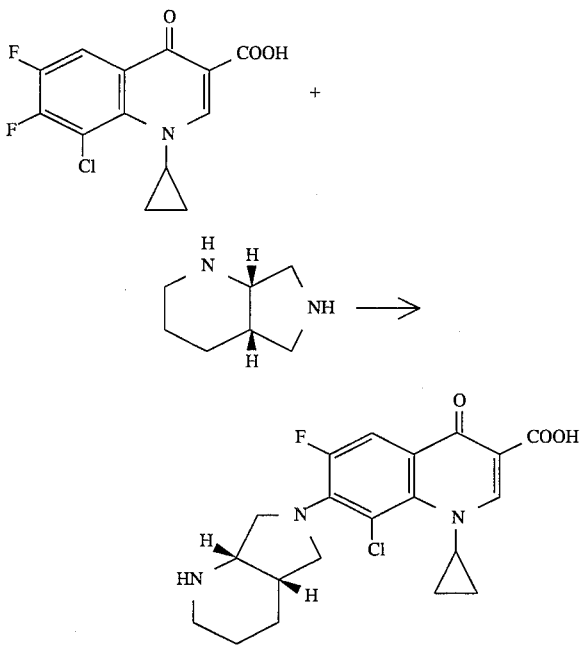

As enantiomerically pure compounds, the bicyclic amines (V) are novel. They may be prepared according to the following processes:

The racemic bicyclic amines (a)

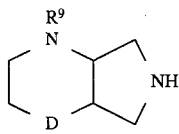
(a)

in which
D represents O or CH$_2$ and
R$^9$ represents H, CH$_3$ or C$_2$H$_5$,
can be reacted with enantiomerically pure acids, e.g. carboxylic acids or sulphonic acids, such as N-acetyl-L-glutamic acid, N-benzoyl-L-alanine, 3-bromo-camphor- 9-sulphonic acid, camphor-3-carboxylic acid, cis-camphoric acid, camphor-10-sulphonic acid, O,O'-dibenzoyl-tartaric acid, D- or L-tartaric acid, mandelic acid, α-methoxy-phenylacetic acid, 1-phenyl-ethane-sulphonic acid or α-phenyl-succinic acid, to give a mixture of the diastereomeric salts, which can be separated into the diastereomerically pure salts by fractional crystallisation (see P. Newman, Optical Resolution Procedures for Chemical Compounds, Volume 1). The molar ratio between amine and enantiomerically pure acid can be varied over a relatively wide range. The enantiomerically pure amines can be liberated by treating these salts with alkali metal or alkaline earth metal hydroxides.

In a similar manner to that described under 1., a racemate resolution of the basic intermediates which arise during preparation of the racemic bicyclic amines can be carried out using the above-listed enantiomerically pure acids. Examples of such basic intermediates are:

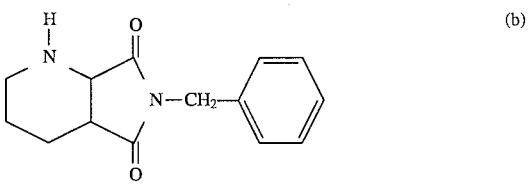
(b)

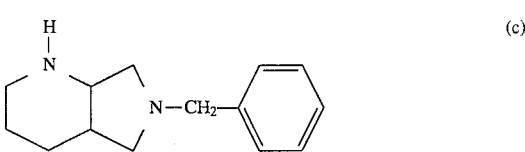
(c)

(d)

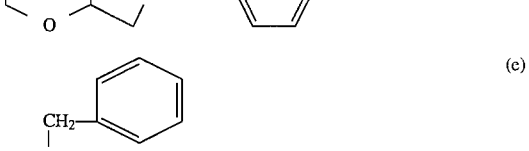
(e)

As an example of a racemate resolution, the separation of 8-benzyl-cis-2,8-diazabicyclo[4.3.0]nonane via the tartrates into the enantiomers and their conversion into the enantiomerically pure cis-2,8-diazabicyclo[ 4.3.0]nonanes may be depicted in the following formula scheme:

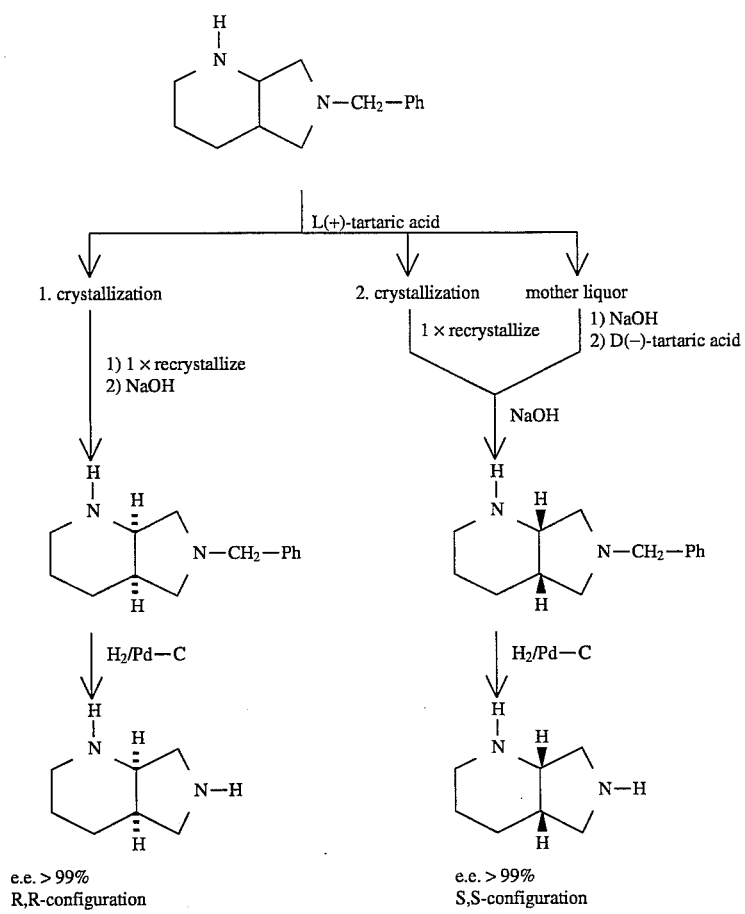

e.e. > 99%
R,R-configuration e.e. > 99%
S,S-configuration

3. Both the racemic amines (a) and the basic intermediates (b)–(e) can, optionally after acylation, be separated by chromatography on chiral carrier materials (see, e.g., G. Blaschke, Angew. Chem. 92, 14 [1980]).

4. Both the racemic amines (a) and the basic intermediates (b), (c) and (e) can, by chemical linkage to chiral acyl radicals, be converted into diastereomeric mixtures which can be separated, by distillation, crystallisation or chromatography, into the diastereomerically pure acyl derivatives from which the enantiomerically pure amines can be isolated by hydrolysis. Examples of reagents for the linkage to chiral acyl radicals are: α-methoxy-α-trifluoromethyl-phenylacetyl chloride, menthyl isocyanate, D- or L-α-phenyl-ethyl isocyanate, menthyl chloroformate and camphor-10-sulphonyl chloride.

5. Chiral instead of achiral protective groups can be introduced during the course of the synthesis of the bicyclic amines (a). In this way, diastereomers are obtained which can be separated. For example, during the synthesis of cis-2,8-diazabicyclo[4.3.0]nonane the benzyl residue can be replaced by the α-phenyl-ethyl radical with the R or S configuration:

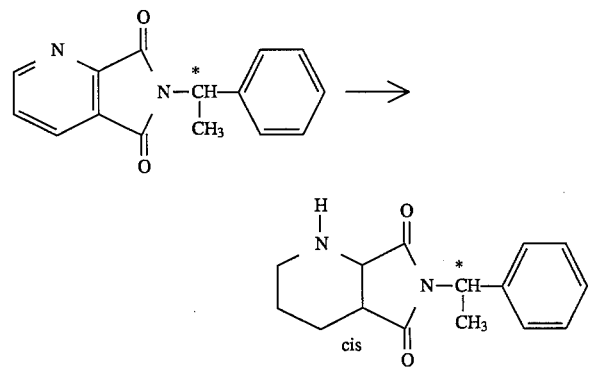

6. The enantiomerically pure amines (VI) can also be constructed from enantiomerically pure precursors, such as, e.g., [R,R]- or [S,S]-3,4-dihydroxypyrrolidine, which should be protected by a protective group on the nitrogen.

The following formula scheme may be given as an example of the synthesis of an enantiomerically pure amine, starting from enantiomerically pure 1-benzyl-3,4-dihydroxy-pyrrolidine:

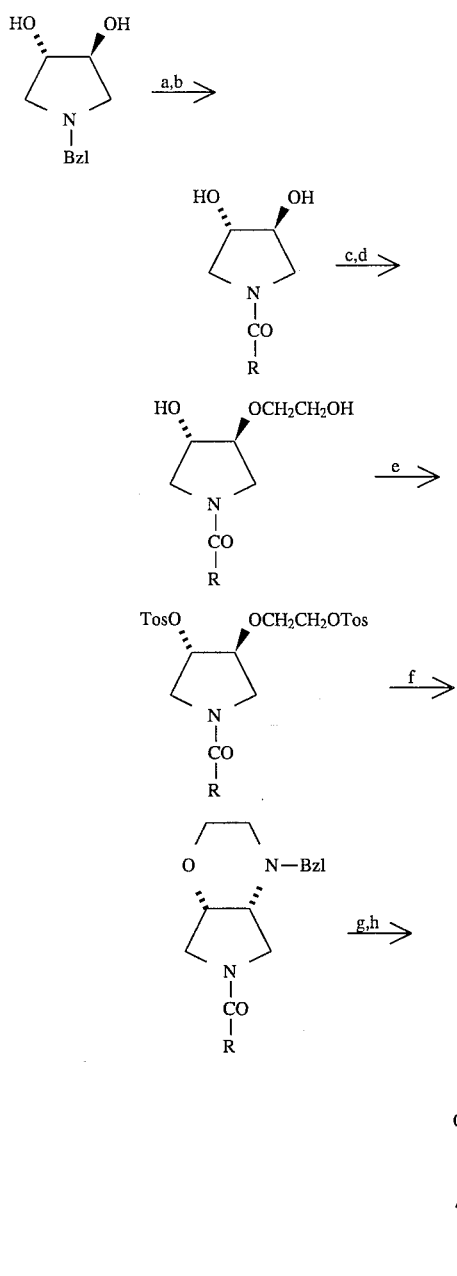

R=for example $(CH_3)_3C-O$,
a: $H_2$, Pd/activated charcoal
b: acylation
c: NaH, $BrCH_2COOC_2H_5$
d: $LiBH_4$
or
c: $CH_2=CH-CH_2Br$, NaH, d: $O_3$, $NaBH_4$,
e: tosyl chloride, $NEt_3$,
f: benzylamine, xylene, reflux
g: hydrolysis
h: $H_2$, Pd/activated charcoal Examples of compounds of the formula (V) which may be mentioned are:

cis-2,8-diazabicyclo[4.3.0]nonane,
cis-2-oxa-5,8-diazabicyclo[4.3.0]nonane,
trans-2-oxa-5,8-diazabicyclo[4.3.0]nonane,
S,S-2,8-diazabicyclo[4.3.0]nonane,
1R,6S-2-oxa-5,8-diazabicyclo[4.3.0]nonane,
1S,6R-2-oxa-5,8-diazabicyclo[4.3.0]nonane,
1R,6R-2-oxa-5,8-diazabicyclo[4.3.0]nonane,
1S,6S-2-oxa-5,8-diazabicyclo[4.3.0]nonane.

The reaction of (IV) with (V), in which the compounds (V) may also be employed in the form of their salts, such as, e.g., the hydrochlorides, is preferably undertaken in a diluent, such as dimethyl sulphoxide, N,N-dimethylformamide, N-methylpyrrolidone, hexamethylphosphoric triamide, sulpholane, acetonitrile, water, an alcohol, such as methanol, ethanol, n-propanol, isopropanol or glycol monomethyl ether, or pyridine. Mixtures of these diluents may likewise be used.

All customary inorganic and organic acid-binding agents can be used as acid binders. These preferably include the alkali metal hydroxides, alkali metal carbonates, organic amines and amidines. Those which may be mentioned specifically as being particularly suitable are: triethylamine, 1,4-diazabicyclo[2.2.2]octane (DABCO), 1,8-diazabicyclo[5.4.0]undec-7-ene (DBU) or excess amine (V).

The reaction temperatures may be varied over a relatively wide range. In general, temperatures of between about 20° and 200° C., preferably of between 80° and 180° C., are employed.

The reaction can be carried out under atmospheric pressure, but also under elevated pressure. In general, pressures of between about 1 and 100 bar, preferably of between 1 and 10 bar, are employed.

In carrying out this process, 1 to 15 mol, preferably 1 to 6 mol, of the compound (V) are employed per 1 mol of the compound (IV).

The following may be mentioned as examples of intermediate compounds of the formula (II) which can be used both as racemates and as enantiomerically pure or diastereomerically pure compounds:

| $R^1$ | $R^2$ | $R^9$ | $X^2$ | D | A |
|---|---|---|---|---|---|
| Cyclopropyl | $C_2H_5$ | H | H | $CH_2$ | C—H |
| $F-CH_2CH_2$ | H | H | H | $CH_2$ | C—F |
| Cyclopropyl | $C_2H_5$ | H | H | $CH_2$ | C—Cl |
| Cyclopropyl | H | H | H | $CH_2$ | C—$OCH_3$ |
| Cyclopropyl | H | H | H | $CH_2$ | C—$CH_3$ |
| Cyclopropyl | $C_2H_5$ | H | H | $CH_2$ | N |
| Cyclopropyl | H | H | Br | $CH_2$ | C—F |
| Cyclopropyl | H | H | Cl | $CH_2$ | C—F |
| Cyclopropyl | H | H | $CH_3$ | $CH_2$ | C—F |
| Cyclopropyl | $C_2H_5$ | H | $NH_2$ | $CH_2$ | C—F |
| Cyclopropyl | H | $CH_3$ | H | $CH_2$ | C—H |
| Cyclopropyl | $C_2H_5$ | $CH_3$ | H | $CH_2$ | C—F |
| Cyclopropyl | H | $CH_3$ | H | $CH_2$ | C—Cl |
| $C_2H_5$ | H | $C_2H_5$ | H | $CH_2$ | C—F |
| Cyclopropyl | H | H | H | O | C—$CH_3$ |
| Cyclopropyl | H | H | H | O | N |
| Cyclopropyl | H | H | Br | O | C—F |

(II)

-continued

| R¹ | R² | R⁹ | X² | D | A |
|---|---|---|---|---|---|
| Cyclopropyl | H | H | Cl | O | C—F |
| Cyclopropyl | H | H | CH₃ | O | C—F |
| Cyclopropyl | H | H | NH₂ | O | C—F— |

(II)

| R¹ | R² | R⁹ | X² | D | A |
|---|---|---|---|---|---|
| Cyclopropyl | CH₃ | H | H | CH₂ | C—H |
| Cyclopropyl | CH₂CH₂F | H | H | CH₂ | C—F |
| Cyclopropyl | CH₂CH₂OH | H | H | CH₂ | C—Cl |
| Cyclopropyl | H | H | H | CH₂ | C—OCH₃ |
| Cyclopropyl | H | H | H | CH₂ | C—CH₃ |
| Cyclopropyl | H | H | H | CH₂ | N |
| Cyclopropyl | H | CH₃ | H | CH₂ | C—F |
| Cyclopropyl | H | H | F | CH₂ | C—F |
| Cyclopropyl | H | C₂H₅ | H | CH₂ | C—F |
| Cyclopropyl | H | H | NH₂ | CH₂ | C—F |
| Cyclopropyl | H | H | H | O | C—H |
| Cyclopropyl | CH₃ | H | H | O | C—F |
| C₂H₅ | H | H | H | O | C—Cl |
| Cyclopropyl | H | C₂H₅ | H | O | C—F |
| Cyclopropyl | H | H | H | O | C—CH₃ |
| Cyclopropyl | H | H | H | O | N |
| Cyclopropyl | H | CH₃ | H | O | C—F |
| Cyclopropyl | H | H | Cl | O | C—F |
| Cyclopropyl | H | H | CH₃ | O | C—F |
| C₂H₅ | H | H | NH₂ | O | C—F |

(II)

| R¹ | R² | R⁹ | X² | D | A |
|---|---|---|---|---|---|
| Cyclopropyl | H | H | H | CH₂ | C—H |
| Cyclopropyl | H | H | H | CH₂ | C—F |
| Cyclopropyl | H | H | H | CH₂ | C—Cl |
| Cyclopropyl | H | H | H | CH₂ | C—OCH₃ |
| Cyclopropyl | H | H | H | CH₂ | C—CH₃ |
| Cyclopropyl | H | H | H | CH₂ | N |
| Cyclopropyl | H | H | Br | CH₂ | C—F |
| Cyclopropyl | H | H | F | CH₂ | C—F |
| Cyclopropyl | H | H | CH₃ | CH₂ | C—F |
| Cyclopropyl | H | H | NH₂ | CH₂ | C—F |
| Cyclopropyl | H | H | H | O | C—H |
| Cyclopropyl | H | H | H | O | C—F |
| Cyclopropyl | H | H | H | O | C—Cl |
| Cyclopropyl | H | CH₃ | H | O | C—F |
| Cyclopropyl | H | C₂H₅ | H | O | C—F |
| Cyclopropyl | H | H | H | O | N |
| Cyclopropyl | H | H | Br | O | C—F |
| Cyclopropyl | H | H | F | O | C—F |
| Cyclopropyl | H | H | CH₃ | O | C—F |
| Cyclopropyl | H | H | NH₂ | O | C—F |

(II)

| R¹ | R² | R⁹ | X² | D | A |
|---|---|---|---|---|---|
| Cyclopropyl | H | H | H | CH₂ | C—H |
| Cyclopropyl | H | H | H | CH₂ | C—F |
| Cyclopropyl | H | H | H | CH₂ | C—Cl |
| Cyclopropyl | H | H | H | CH₂ | C—OCH₃ |
| Cyclopropyl | H | H | H | CH₂ | C—CH₃ |
| Cyclopropyl | H | H | H | CH₂ | N |
| Cyclopropyl | H | H | Br | CH₂ | C—F |
| Cyclopropyl | H | H | F | CH₂ | C—F |
| Cyclopropyl | H | H | CH₃ | CH₂ | C—F |
| Cyclopropyl | H | H | NH₂ | CH₂ | C—F |
| Cyclopropyl | H | H | H | O | C—H |
| Cyclopropyl | H | H | H | O | C—F |
| Cyclopropyl | H | H | H | O | C—Cl |
| Cyclopropyl | H | CH₃ | H | O | C—F |
| Cyclopropyl | H | C₂H₅ | H | O | C—F |
| Cyclopropyl | H | H | H | O | N |
| Cyclopropyl | H | H | Br | O | C—F |
| Cyclopropyl | H | H | F | O | C—F |
| Cyclopropyl | H | H | CH₃ | O | C—F |
| Cyclopropyl | H | H | NH₂ | O | C—F |

(II)

| R¹ | R² | R⁹ | X² | D | A |
|---|---|---|---|---|---|
| 2,4-Difluorphenyl | H | H | Cl | CH₂ | C—F |
| 2,4-Difluorphenyl | H | H | CH₃ | CH₂ | C—F |
| 2,4-Difluorphenyl | H | CH₃ | H | CH₂ | C—F |
| 2,4-Difluorphenyl | H | H | H | O | C—F |
| 2,4-Difluorphenyl | H | H | H | O | C—Cl |
| 4-Fluorphenyl | H | H | H | O | CH |
| 2,4-Difluorphenyl | H | H | H | O | N |
| 2,4-Difluorphenyl | H | H | H | O | C—OCH₃ |
| 2,4-Difluorphenyl | H | C₂H₅ | H | O | C—F |
| 2,4-Difluorphenyl | H | H | H | CH₂ | C—F |
| 2,4-Difluorphenyl | H | H | F | CH₂ | C—F |
| 2,4-Difluorphenyl | H | H | H | CH₂ | C—Cl |
| 2,4-Difluorphenyl | H | H | H | O | C—Cl |
| 2,4-Difluorphenyl | H | H | H | CH₂ | N |
| 2,4-Difluorphenyl | H | H | H | O | N |
| 2,4-Difluorphenyl | H | H | H | O | C—H |
| 2,4-Difluorphenyl | C₂H₅ | H | H | O | C—F |

The starting compounds of the structures (III) are known, or can be prepared by known methods. As an example may be mentioned:

Benzhydryl 6R,7R-3-chloromethyl-8-oxo-7-phenylacetylamino- 5-thia-1-aza-bicyclo[4.3.0]oct-2-ene-2-carboxylate.

The reaction of (II) with (III) is preferably undertaken in a diluent, such as dimethyl sulphoxide, N,N-dimethyl-formamide, N-methylpyrrolidone, hexamethylphosphoric triamide, sulpholane, acetonitrile, acetone, water, an alcohol, such as methanol, ethanol, n-propanol, isopropanol or glycol monomethyl ether, or pyridine, and in the presence of an acid binder. Mixtures of these diluents may likewise be used.

All customary inorganic and organic acid-binding agents can be used as acid binders. These preferably include the alkali metal hydroxides, alkali metal carbonates, organic amines and amidines. Those which may be mentioned specifically as being particularly suitable are: triethylamine, 1,4-diazabicyclo[2.2.2]octane (DABCO), 1,8-diazabicyclo[5.4.0]undec-7-ene (DBU) or excess amine (VI).

The reaction of (II) with (III) can also be carried out after silylation of the compound of the formula (II) with a silylating agent, such as, for example, trimethylchlorosilane, bis-(trimethylsilyl)acetamide, N-(trimethylsilyl)-trifluoroacetamide or hexamethyldisilazane, without further addition of an auxiliary base.

The radicals which are customary in β-lactam chemistry are used as protective groups for blocking reactive groups, such as, for example, amino groups, hydroxyl groups, thiol groups or carboxyl groups. The following may be mentioned by way of example (for details, see J. W. F. McOmie, Protective Groups in Organic Chemistry (1973), T. W. Greene, Protective Groups in Organic Synthesis (1981):

a) for the protection of amino groups: tert-butoxycarbonyl, allyloxycarbonyl, isopropenyloxycarbonyl, trichloroethoxycarbonyl, 4-nitrobenzyloxycarbonyl, trichloroacetyl, trifluoroacetyl, trityl and trimethylsilyl b) for the protection of hydroxyl groups: acetyl, trimethylsilyl and tetrahydropyranyl c) for the protection of carboxyl groups: ester groups, such as benzhydryl, 4-methoxybenzyl, 4-nitrobenzyl, acetoxymethyl and tert-butyl ester.

The reaction temperatures may be varied over a relatively wide range. In general, temperatures of between about 0° and 80° C., preferably of between 20° and 50° C., are employed.

The reaction can be carried out under atmospheric pressure, but also under elevated pressure. In general, pressures of between about 1 and 100 bar, preferably of between 1 and 10 bar, are employed.

In carrying out this process, 1 to 5 mol, preferably 1 to 2 mol, of the compound (III) are employed per 1 mol of the compound (II).

The preparation of the acid-addition salts of the compounds according to the invention takes place in a customary manner, for example by dissolving the betaine in aqueous acid and precipitating the salt with an organic solvent which is miscible with water, such as methanol, ethanol, acetone or acetonitrile. Equivalent quantities of betaine and acid can also be heated in water or an alcohol, such as glycol monomethyl ether, and the solution subsequently evaporated to dryness, or the precipitated salt filtered off with suction. Pharmaceutically utilisable salts are to be understood to mean, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in a sub-equivalent quantity of alkali metal hydroxide solution or alkaline earth metal hydroxide solution, filtering off undissolved betaine, and evaporating the filtrate to dryness. Sodium, potassium or calcium salts are pharmaceutically suitable. The corresponding silver salts are obtained by reacting an alkali metal or alkaline earth metal salt with a suitable silver salt, such as silver nitrate.

Besides the active compounds mentioned in the examples, the compounds listed in the following tables, for example, can also be prepared by the processes described. The compounds according to the invention can exist both as racemates and as enantiomerically pure or diastereomerically pure compounds:

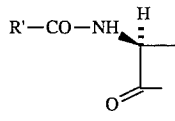

| R' | A | X² | D |
|---|---|---|---|
| 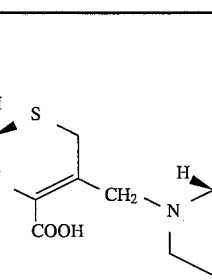 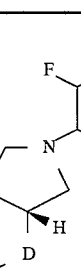 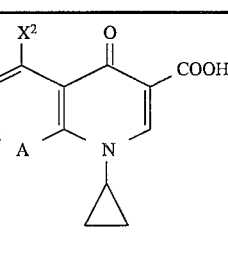 | CF | H | CH₂ |
| | CF | F | CH₂ |
| | CF | NH₂ | CH₂ |
| | C—OCH₃ | H | CH₂ |
| | N | H | CH₂ |
| | CCl | H | O |
| | CCl | H | CH₂ |
| | CF | H | CH₂ |

-continued

| R' | A | X² | D |
|---|---|---|---|
| 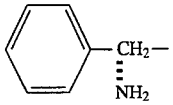 | CH<br>CCl<br>CF | H<br>H<br>H | CH₂<br>CH₂<br>CH₂ |
| 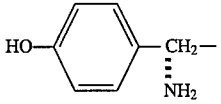 | CH<br>CCl<br>CF | H<br>H<br>H | CH₂<br>CH₂<br>CH₂ |
| 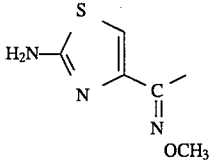 | CH<br>CF<br>CCl<br>N<br>CF | H<br>H<br>H<br>H<br>H | CH₂<br>CH₂<br>CH₂<br>CH₂<br>O |
| 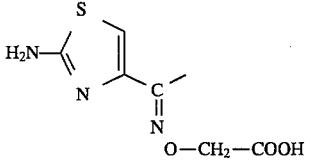 | CF<br>CF<br>CCl | H<br>F<br>H | CH₂<br>CH₂<br>CH₂ |
| 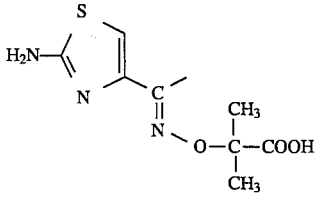 | CF<br>CF<br>CCl | H<br>F<br>H | CH₂<br>CH₂<br>CH₂ |
| 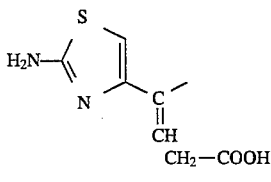 | CH<br>CF<br>CCl | H<br>H<br>H | CH₂<br>CH₂<br>CH₂ |
| 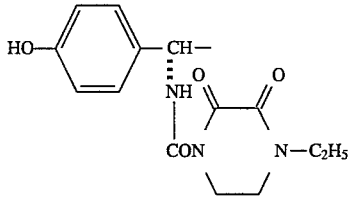 | CH<br>CF<br>CCl<br>N | H<br>H<br>H<br>H | CH₂<br>CH₂<br>CH₂<br>CH₂ |
| 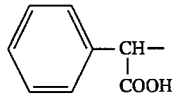 | CH<br>CF<br>CCl | H<br>H<br>H | CH₂<br>CH₂<br>CH₂ |

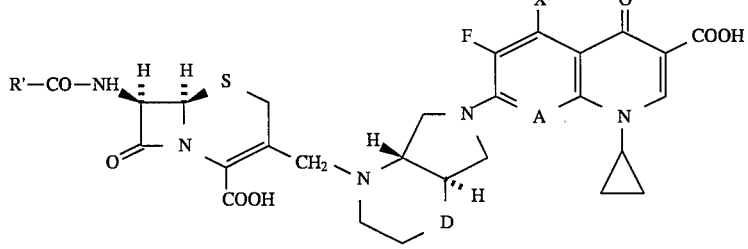

-continued
| R' | A | X² | D | |
|---|---|---|---|---|
| 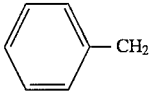 | | CCl | H | CH₂ |
| | | CF | H | CH₂ |
| | | CF | F | CH₂ |
| | | CF | NH₂ | CH₂ |
| | | CF | H | O |
| | | CH | H | O |
| | | CCl | H | O |
| 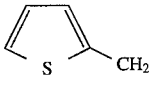 | | CCl | H | CH₂ |
| | | CCl | H | O |
| | | CF | H | CH₂ |
| | | CF | H | O |
| 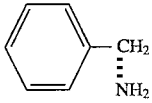 | | CCl | H | CH₂ |
| | | CCl | H | O |
| | | CF | H | CH₂ |
| | | CF | H | O |
| 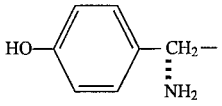 | | CH | H | CH₂ |
| | | CCl | H | CH₂ |
| | | CF | H | CH₂ |
| | | CF | H | O |
| 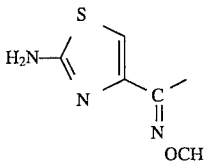 | | CH | H | CH₂ |
| | | CF | H | CH₂ |
| | | CCl | H | CH₂ |
| | | N | H | CH₂ |
| | | CF | H | O |
| 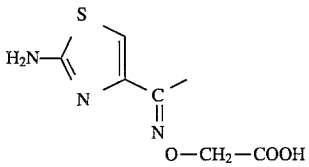 | | CF | H | CH₂ |
| | | CF | H | O |
| | | CF | NH₂ | CH₂ |
| | | CCl | H | CH₂ |
| 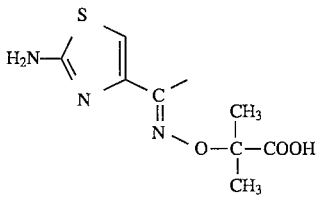 | | CF | H | CH₂ |
| | | CF | H | O |
| | | CF | F | CH₂ |
| | | CCl | H | CH₂ |
| 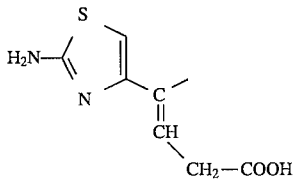 | | CH | H | CH₂ |
| | | CF | H | CH₂ |
| | | CF | H | O |
| | | CCl | H | CH₂ |
| 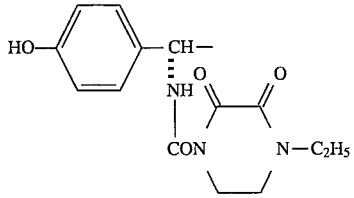 | | CH | H | CH₂ |
| | | CF | H | CH₂ |
| | | CF | H | O |
| | | CCl | H | CH₂ |
| | | N | H | CH₂ |
| 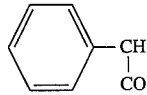 | | CH | H | CH₂ |
| | | CF | H | CH₂ |
| | | CF | H | O |
| | | CCl | H | CH₂ |

-continued

| R' | A | $X^2$ | D |
|---|---|---|---|

[Structure: R'—CO—NH attached to β-lactam-thiazine fused with pyrrolidine linker to quinolone core bearing $X^2$, F, cyclopropyl N, COOH, with positions labeled A and D]

| R' | A | $X^2$ | D |
|---|---|---|---|
| phenyl-CH₂ | CCl | H | CH₂ |
| | CF | H | CH₂ |
| | CF | F | CH₂ |
| | CF | NH₂ | CH₂ |
| | CF | H | O |
| | CH | H | O |
| | CCl | H | O |
| thienyl-CH₂ | CCl | H | CH₂ |
| | CCl | H | O |
| | CF | H | CH₂ |
| | CF | H | O |
| phenyl-CH(NH₂)— | CH | H | CH₂ |
| | CH | H | O |
| | CCl | H | CH₂ |
| | CCl | H | O |
| | CF | H | CH₂ |
| | CF | H | O |
| HO-phenyl-CH(NH₂)— | CH | H | CH₂ |
| | CCl | H | CH₂ |
| | CF | H | CH₂ |
| | CF | H | O |
| H₂N-thiazolyl-C(=N-OCH₃)— | CH | H | CH₂ |
| | CF | H | CH₂ |
| | CCl | H | CH₂ |
| | N | H | CH₂ |
| | CF | H | O |
| H₂N-thiazolyl-C(=N-O-CH₂-COOH)— | CF | H | CH₂ |
| | CF | H | O |
| | CF | NH₂ | CH₂ |
| | CCl | H | CH₂ |
| H₂N-thiazolyl-C(=N-O-C(CH₃)₂-COOH)— | CF | H | CH₂ |
| | CF | H | O |
| | CF | F | CH₂ |
| H₂N-thiazolyl-C(=CH-CH₂-COOH)— | CCl | H | CH₂ |
| | CH | H | CH₂ |
| | CF | H | CH₂ |
| | CF | H | O |
| | CCl | H | CH₂ |

-continued

| R' | A | X² | D | |
|---|---|---|---|---|
| 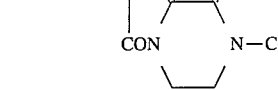 | | CH<br>CF<br>CF<br>CCl<br>N | H<br>H<br>H<br>H<br>H | CH₂<br>CH₂<br>O<br>CH₂<br>CH₂ |
| 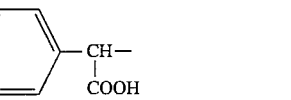 | | CH<br>CF<br>CF<br>CCl<br>CCl | H<br>H<br>H<br>H<br>H | CH₂<br>CH₂<br>O<br>CH₂<br>CH₂ |

| | | CCl<br>CF<br>CF<br>CF<br>CH<br>N<br>CCl | H<br>H<br>F<br>H<br>H<br>H<br>H | CH₂<br>CH₂<br>CH₂<br>O<br>CH₂<br>CH₂<br>O |
|---|---|---|---|---|
| 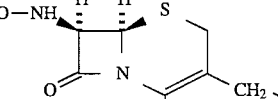 | | | | |
|  | | CCl<br>CF | H<br>H | CH₂<br>CH₂ |
| 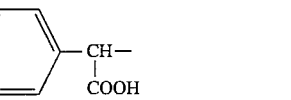 | | CH<br>CCl<br>CF | H<br>H<br>H | CH₂<br>CH₂<br>CH₂ |
| 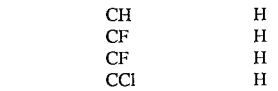 | | CH<br>CCl<br>CF<br>CF | H<br>H<br>H<br>H | CH₂<br>CH₂<br>CH₂<br>O |
|  | | CH<br>CF<br>CCl<br>N<br>CF | H<br>H<br>H<br>H<br>H | CH₂<br>CH₂<br>CH₂<br>CH₂<br>O |
|  | | CF<br>CF<br>CCl | H<br>NH₂<br>H | CH₂<br>CH₂<br>CH₂ |

-continued

| R' | A | X² | D |
|---|---|---|---|
| H₂N-[thiazole]-C(=N-O-C(CH₃)₂-COOH)- | CF | H | CH₂ |
|  | CF | F | CH₂ |
|  | CCl | H | CH₂ |
| H₂N-[thiazole]-C(=CH-CH₂-COOH)- | CH | H | CH₂ |
|  | CF | H | CH₂ |
|  | CCl | H | CH₂ |
| HO-C₆H₄-CH(NH-CON[piperazinyl-N-C₂H₅](=O)(=O))- | CH | H | CH₂ |
|  | CF₂ | H | CH₂ |
|  | CCl | H | CH₂ |
|  | N | H | CH₂ |
| C₆H₅-CH(COOH)- | CH | H | CH₂ |
|  | CF | H | CH₂ |
|  | CCl | H | CH₂ |

The compounds according to the invention have a strong antibiotic effect and, while being of low toxicity, exhibit a broad antibacterial spectrum against Gram-positive positive and Gram-negative organisms, in particular against enterobacteria; in particular against those which are resistant to several antibiotics, such as, e.g., penicillins, cephalosporins, aminoglycosides, sulphonamides, tetracyclines and quinolones.

These valuable properties permit their use as chemotherapeutic active compounds in medicine, and as compounds for preserving inorganic and organic materials, in particular organic materials of all kinds, e.g. polymers, lubricants, paints, fibres, leather, paper and wood, foodstuffs and water.

The compounds according to the invention are effective against a very broad spectrum of microorganisms. With their help, Gram-negative and Gram-positive bacteria and bacteria-like microorganisms can be controlled, and the diseases caused by these pathogens can be prevented, ameliorated and/or cured.

The compounds according to the invention are distinguished by an amplified effect on dormant and resistant microorganisms. In the case of dormant bacteria, that is bacteria which show no detectable growth, the compounds have an effect at concentrations which are well below those of hitherto known substances. This refers not only to the quantity to be employed, but also to the speed of killing. It was possible to observe results of this kind in the case of Gram-positive and Gram-negative bacteria, in particular in the case of *Staphylococcus aureus*, *Pseudomonas aeruginosa*, *Enterococcus faecalis* and *Escherichia coli*.

The compounds according to the invention also exhibit surprising increases in effect against bacteria, in particular resistant *Staphylococcus aureus*, *Escherichia coli*, *Pseudomonas aeruginosa* and *Enterococcus faecalis*, which are categorised as being less sensitive towards comparable substances.

The compounds according to the invention are particularly effective against bacteria and bacteria-like microorganisms. They are therefore particularly well suited for the prophylaxis and chemotherapy of local and systemic infections which are caused by these pathogens in human and veterinary medicine.

The compounds according to the invention can be used in various pharmaceutical preparations. Preferred pharmaceutical preparations which may be mentioned are tablets, coated tablets, capsules, pills, granules, suppositories, solutions, suspensions and emulsions, pastes, ointments, gels, creams, lotions, powders and sprays.

The determination of the "minimum inhibitory concentrations" (MIC) was effected in mitrotitre plates using brain-heart infusion broth, with about $10^5$ microorganisms/ml being employed as the inoculum.

The table below verifies the surprising advantages of the compound A according to the invention (compound from Example 2) in comparison with the reference compound B (compound from Example 15 of EP 492 277):

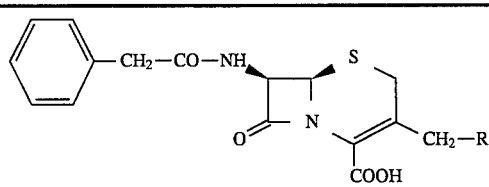

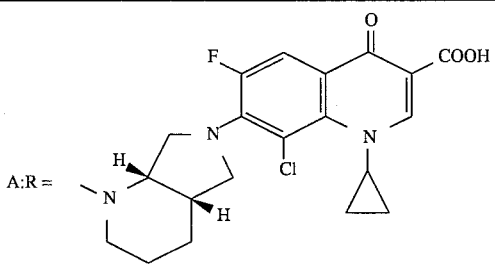

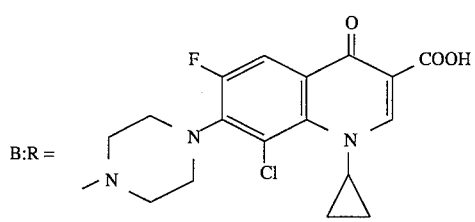

Table = MIC values (μg/ml)

| Test strain | Compound A | Reference compound B |
| --- | --- | --- |
| *Escherichia coli* Neumann | 0.03 | 0.25 |
| Klebsiella sp. 63 | 0.125 | 1 |
| *Serratia marcescens* 16040 | 4 | 16 |
| *Staphylococcus aureus* | | |
| ICB 25701 | 0.25 | 32 |
| ICB 25768 | 2 | 128 |
| 1756 | 0.004 | 0.03 |
| 133 | 0.03 | 0.125 |
| *Enterococcus faecalis* | | |
| 27101 | 0.25 | 8 |
| 9790 | 0.25 | 8 |

Preparation of the precursors

EXAMPLE A

[S,S]-2,8-Diazabicyclo[4.3.0]nonane

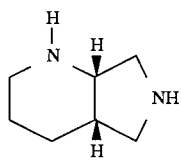

1) [S,S]-8-Benzyl-2,8-diazabicyclo[4.3.0]nonane
Method I:
a) Separation of the diastereomeric salts:
3.0 g (20 mmol) of D(−)-tartaric acid are dissolved in 10 ml of dimethylformamide by heating to 80° C., and a solution of 2.16 g (10 mmol) of cis-8-benzyl-2,8-diazabicyclo[4.3.0]nonane in 3 ml of dimethylformamide is added. The mixture is subsequently stirred at 0° C. for 1 hour, and then it is filtered with suction, washing with dimethylformamide and methoxyethanol.

Yield: 1.93 g, Melting point: 146°–151° C., $[\alpha]_D^{23}$=−19.3° (c=1, H$_2$O).

Diastereomerically pure [S,S]-8-benzyl-2,8-diazabicyclo[4.3.0]nonane D-tartrate is obtained by a single recrystallisation from methoxyethanol.

$[\alpha]_D^{23}$=−22.7° (c=1, H$_2$O), Melting point: 148°–154° C.
b) Liberation of the base:
40 g of [S,S]-8-benzyl-2,8-diazabicyclo[4.3.0]nonane D-tartrate are dissolved in 250 ml of water, and 32 g of 45% strength sodium hydroxide solution are added. The precipitated oil is taken up in 150 ml of tert-butyl methyl ether, the aqueous phase is extracted once more with 150 ml of tert-butyl methyl ether, and the combined organic phases are concentrated after drying over sodium sulphate. Distillation then takes place in vacuo.

Yield: 18.5 g of [S,S]-8-benzyl-2,8-diazabicyclo[ 4.3.0] nonane, Boiling point: 107°–109° C./0.1 mbar, $[\alpha]_D^{24}$17.3° (undiluted).
Method II:
75.0 g (0.5 mol) of L(+)-tartaric acid are dissolved at 80° C. in 250 ml of dimethylformamide, and 54.1 g (0.25 mol) of cis-8-benzyl-2,8-diazabicyclo[4.3.0]nonane, as a solution in 75 ml of dimethylformamide, are added dropwise. The mixture is cooled slowly down to 20° C., and the crystal suspension is subsequently stirred for 1 hour. The crystals ([R,R]-8-benzyl-2,8-diazabicyclo 4.3.0]nonane L-tartrate) are filtered off with suction, and the filtrate is concentrated in a rotary evaporator. The residue is dissolved in 500 ml of water and worked up with 63 g of 45% strength sodium hydroxide solution as described under method I.

Yield: 25.2 g of [S,S]-8-benzyl-2,8-diazabicyclo[4.3.0]nonane; the product contains 3.6% of the R,R-enantiomer (determined by gas chromatography after derivatisation with menthyl chloroformate).

The compound can be reacted by method I with D(−)-tartaric acid to give diastereomerically pure [S,S]-8-benzyl-2,8-diazabicyclo[4.3.0]nonane D-tartrate. In this case, recrystallisation is not necessary.
Method III:
73.6 g (0.34 mol) of cis-8-benzyl-2,8-diazabicyclo[4.3.0]nonane, as a solution in 111 ml of dimethylformamide, are added dropwise, at 80° to 90° C., to a solution of 102.9 g (0.685 mol) of L(+)-tartaric acid in 343 ml of dimethylformamide. Seeding with [R,R]-8-benzyl-2,8-diazabicyclo[ 4.3.0]nonane L-tartrate takes place, and the mixture is cooled slowly down to an internal temperature of 18° C. The crystals are filtered off with suction, and the filtrate is seeded with [S,S]-8-benzyl-2,8-diazabicyclo[ 4.3.0]nonane L-tartrate and stirred until crystallisation is complete. (After concentrating and liberating the base as described under method I, [S,S]-8-benzyl-2,8-diazabicyclo[4.3.0]nonane D-tartrate can be obtained from the mother liquor by purification with D(−)-tartaric acid.) Subsequently, filtration takes place with suction, and the sediment is washed with dimethylformamide and isopropanol and air-dried. The crystals are recrystallised from 88% strength ethanol. 52 g of [S,S]-8-benzyl- 2,8-diazabicyclo[4.3.0]nonane L-tartrate trihydrate are obtained.

Melting point: 201°–204° C., $[\alpha]_D^{23}$=+5.2° (c=1, H$_2$O).

The salt can be processed as described under method I (liberation of the base) to give enantiomerically pure S,S]-8-benzyl-2,8-diazabicyclo[4.3.0]nonane.
Method IV:
a) Separation of cis-8-benzyl-7,9-dioxo-2,8-diazabicyclo[ 4.3.0]nonane enantiomers to give [1S,6R]-8-benzyl- 7,9-dioxo-2,8-diazabicyclo[4.3.0]nonane The procedure is analogous to Example B (method II/a), with D(−)-tartaric acid being used as the chiral auxiliary reagent, or else the procedure is as follows:

Mother liquor and washings from [1R,6S]-8-benzyl-7,9-dioxo-2,8-diazabicyclo[4.3.0]nonane L-tartrate (from Example B, method II/a) are concentrated together, taken up in water, and extracted three times with toluene. The toluene phases are discarded. Saturated sodium hydrogen carbonate solution is added to the aqueous phase until a pH of 7 to 8 is reached, and the mixture is subsequently extracted four times with methylene chloride. The combined methylene chloride phases are dried over magnesium sulphate and concentrated.

Yield: 14.4 g (60% of theory of the racemic cis-8-benzyl-7,9-dioxo-2,8-diazabicyclo[4.3.0]nonane originally employed). [α]$_D^{23}$: −4.5° (c=5, ethanol).

These 14.4 g (59 mmol) are crystallised with 8.6 g (57 mmol) of D(−)-tartaric acid from 120 ml of ethanol in analogy with Example B (method II/a).

Yield: 8.9 g (77% of theory) of [1S,6R]-8-benzyl-7,9-dioxo-2,8-diazabicyclo[4.3.0]nonane D-tartrate. [α]$_D^{23}$: −46.2° (c=0.5, 1N HCl); a further purification takes place following recrystallisation from an ethanol/glycol monomethyl ether mixture: [α]$_D^{23}$: −59.3° (c=0.5, 1N HCl).

5.0 g (12.7 mmol) of the diastereomerically pure tartrate obtained in this way were converted into the free amine as described under Example B, method II/a:

Yield: 3.0 g (96% of theory) of [1S,6R]-8-benzyl-7,9-dioxo-2,8-diazabicyclo[4.3.0]nonane, melting point: 60°–61° C., [α]$_D^{23}$: −22.2° (c=5, ethanol).

After derivatisation with menthyl chloroformate, an enantiomeric excessee of 96.6% was determined by gas chromatography.

b) Reduction of [1S,6R]-8-benzyl-7,9-dioxo-2,8-diazabicyclo[ 4.3.0]nonane to give [S,S]-8-benzyl-2,8-diazabicyclo[ 4.3.0]nonane The procedure is analogous to Example B (method II, b), but with [1S,6R]-8-benzyl-7,9-dioxo-2,8-diazabicyclo[ 4.3.0]nonane being employed as the starting material.

The crude product obtained after the working up was found, on derivatisation with menthyl chloroformate, to be [S,S]-8-benzyl-2,8-diazabicyclo[4.3.0]nonane. No racemisation was observed during the reduction.

2) [S,S]-2,8-Diazabicyclo[4.3.0]nonane 28.4 g (0.131 mol) of [S,S]-8-benzyl-2,8-diazabicyclo[ 4.3.0]nonane are hydrogenated in 190 ml of methanol over 5.8 g of palladium on active charcoal (5%) at 90° C. and 90 bar within the space of 5 hours. The catalyst is then filtered off with suction and washed with methanol, and the filtrate is concentrated in a rotary evaporator. The residue is distilled without fractionating.

Yield: 15.0 g (90.5% of theory) of [S,S]-2,8-diazabicyclo [4.3.0]nonane, boiling point: 44°–59° C. 0.18 mbar, [α]$_D^{22}$= −2.29° (undiluted), ee>99% (determined by gas chromatography after derivatisation with Mosher's reagent).

Method V:

3.75 g (25 mmol) of L(+)-tartaric acid are initially introduced dissolved in 50 ml of dimethylformamide at 80° C., and 10.82 g (50 mmol) of cis-8-benzyl-2,8-diazabicyclo[ 4.3.0]nonane, as a solution in 15 ml of dimethylformamide, are added dropwise. Seeding with [R,R]-8-benzyl-2,8-diazabicyclo[4.3.0]nonane L-tartrate takes place, and the mixture is stirred at about 72° C. for one hour in order to complete the formation of crystal nuclei. The mixture is then slowly cooled down to 15° C. and filtered with suction, washing twice with 13 ml of dimethylformamide on each occasion. The combined filtrates are heated to 80° C. and mixed with a further 3.75 g (25 mmol) of L(+)-tartaric acid. The mixture is heated still further to 119° C. until a clear solution is obtained and is then cooled slowly again to room temperature while being seeded with [S,S]-8-benzyl-2,8-diazabicyclo[4.3.0]nonane L-tartrate. The crystals are filtered off with suction, washed successively with dimethylformamide, 2-methoxy-ethanol and ethanol, and air-dried.

Yield: 9.59 g Melting point: 188° to 192° C.

The crystals are recrystallised from 95 ml of 80% strength ethanol. 8.00 g of [S,S]-8-benzyl-2,8-diazabicyclo[4.3.0] nonane L-tartrate trihydrate (76% of theory) are obtained, which melts with frothing at 112° to 118° C., and then solidifies again and melts once more at 199° to 201° C.

[α]$_D^{23}$=−4.5° (c=1, water) ee: 98.0% (determined by gas chromatography after derivatisation with menthyl chloroformate).

EXAMPLE B

[R,R]-2,8-Diazabicyclo[4.3.0]nonane

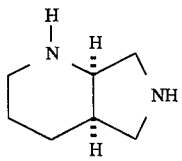

1) [R,R]-8-Benzyl-2,8-diazabicyclo[4.3.0]nonane
Method I:

The crystals of [R,R]-8-benzyl-2,8-diazabicyclo[4.3.0] nonane obtained according to Example A, method II, are washed with dimethylformamide and methoxyethanol (49.2 g) and recrystallised from 300 ml of methoxyethanol. 45.6 g of enantiomerically pure [R,R]-8-benzyl-2,8-diazabicyclo [4.3.0]nonane L-tartrate are obtained (enantiomeric purity determined by gas chromatography after derivatisation with menthyl chloroformate).

Melting point: 121°–124° C., [α]$_D^{23}$=+22.3° (c=1, H$_2$O).

The salt (44.5 g) is converted into the free base as described in Example A, method Ib. 20.2 g of [R,R]-8-benzyl- 2,8-diazabicyclo[4.3.0]nonane are obtained.

Boiling point: 107°–111° C./0.04 mbar, [α]$_D^{24}$=−17.5° (undiluted).
Method II a) Separation of cis-8-benzyl-7,9-dioxo-2,8-diazabicyclo[ 4.3.0]nonane enantiomers to give [1R,6S]-8-benzyl- 7,9-dioxo-2,8-diazabicyclo[4.3.0]nonane 24.1 g (98.8 mmol) of cis-8-benzyl-7,9-dioxo-2,8-diazabicyclo[ 4.3.0]nonane are heated to reflux while stirring in a mixture consisting of 410 ml of ethanol and 25 ml of acetonitrile in a three-necked flask. Subsequently, 14.8 g (98.8 mmol) of L(+)-tartaric acid are added all at once. After the total amount of tartaric acid has dissolved completely, first the heating is turned off but the flask is left in the oil bath. When the system has cooled to such an extent that the solution is no longer boiling, the stirrer is turned off. At a temperature of 50° C., crystallisation takes place on addition of seeding crystals. After standing overnight and cooling to room temperature, the precipitated crystals are filtered off with suction, washed with a little ethanol/petroleum ether (1:1), and dried at 80° C. for 2 hours.

Yield: 9.8 g (50% of theory) of [1R,6S]-8-benzyl-7,9-dioxo-2,8-diazabicyclo[4.3.0]nonane L-tartrate, [α]$_D^{23}$=+ 47.7° (c=0.5, 1N HCl)

The compound can be purified still further by being recrystallised twice from a mixture of ethanol and glycol monomethyl ether:

[α]$_D^{23}$=+58.6° (c=0.5, 1N HCl). $^1$H-NMR (DMSO): 7.22–7.35 (2 m, 2H, aryl-H); 4.55 (s, 2H, benzyl-CH$_2$); 4.28 (s, 2H, tartaric-CH); 3.91 (d, 1H, 1-CH); 2.97 (dd, 1H, 6-CH); 2.53–2.66 (m, 2H, 3-CH$_2$); 1.78 and 1.68 (2 m, 2H, 5-CH$_2$); 1.42 and 1.28 ppm (2 m, 2H, 4-CH$_2$). C$_{18}$H$_{22}$N$_2$O$_8$ (394) Calculated: C 54.4 H 5.6 N 7.1 O32.5 Found: C 54.7 H 5.8 N 7.1 O 32.4

Determination of the absolute configuration was effected by means of an X-ray structural analysis:

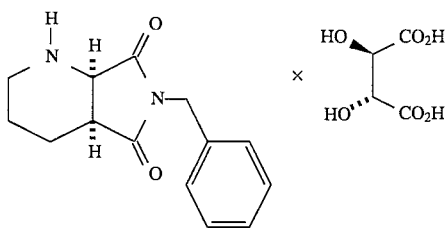

3.6 g (9.1 mmol) of the diastereomerically pure tartrate obtained in this way are dissolved in water to liberate the base and saturated sodium hydrogen carbonate solution is then added until a pH of 7 to 8 is reached. The aqueous solution is extracted four times with 20 ml of methylene chloride on each occasion. The combined methylene chloride phases are dried over magnesium sulphate and concentrated.

Yield: 2.2 g (99% of theory) of [1R,6S]-8-benzyl- 7,9-dioxo-2,8-diazabicyclo[4.3.0]nonane, Melting point: 60°–61° C., $[\alpha]_D^{23}$: +21.8° (c=5, ethanol).

An enantiomeric excessee of 93.8% was determined by gas chromatography after derivatisation with menthyl chloroformate.

b) Reduction of [1R,6S]-8-benzyl-7,9-dioxo-2,8-diazabicyclo[ 4.3.0]nonane to give [R,R]-8-benzyl-2,8-diazabicyclo[ 4.3.0]nonane 0.34 g (9 mmol) of lithium aluminium hydride in 18 ml of anhydrous tetrahydrofuran is initially introduced into a heated flask under $N_2$, and 0.73 g (3 mmol) of [1R,6S]-8-benzyl-7,9-dioxo-2,8-diazabicyclo[ 4.3.0]nonane as a solution in 3 ml of anhydrous tetrahydrofuran is added dropwise. The mixture is then boiled with a reflux condenser for 16 hours. Working up is effected by the dropwise addition of 0.34 ml of water in 10 ml of tetrahydrofuran, 0.34 ml of 10% strength sodium hydroxide solution and 1.02 ml of water. The precipitate is filtered off with suction and washed with tetrahydrofuran, and the filtrate is concentrated. 0.7 g of crude [R,R]-8-benzyl-2,8-diazabicyclo[ 4.3.0]nonane remain (GC content: 99%).

It was not possible to detect any racemisation on determination of the enantiomeric purity by gas chromatography using menthyl chloroformate.

2) [R,R]-2,8-Diazabicyclo[4.3.0]nonane 19.4 g (0.09 mol) of [R,R]-8-benzyl-2,8-diazabicyclo[ 4.3.0]nonane are hydrogenated according to the directions in Example A, 2.

Yield: 9.61 g (85%) of [R,R]-2,8-diazabicyclo[4.3.0] nonane, Boiling point: 45°–58° C./0.08 mbar, $[\alpha]_D^{23}$=+ 2.30° (undiluted).

EXAMPLE C

[S,S]-2-Methyl-2,8-diazabicyclo[4.3.0]nonane

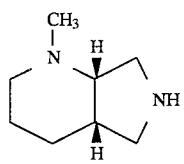

1) [S,S]-8-Benzyl-2-methyl-2,8-diazabicyclo[4.3.0]nonane 20 ml of 37% formaldehyde solution, 40 ml of water and 24 g of acetic acid are added to 43.2 g (0.2 mmol) of [S,S]-8-benzyl-2,8-diazabicyclo[4.3.0]nonane, and the mixture is hydrogenated over 2 g of palladium on active charcoal (5%) at 20° C. and 20 bar for 10 hours. The mixture is then filtered with suction, the filtrate is made alkaline with potassium carbonate, and the product is extracted with tert-butyl methyl ether. After drying over sodium sulphate, the mixture is concentrated and the residue distilled in vacuo.

Yield: 14.8 g, Boiling point: 114°–124° C./0.14 mbar.

2) [S,S]-2-Methyl-2,8-diazabicyclo[4.3.0]nonane 12.9 g (56 mmol) of [S,S]-8-benzyl-2-methyl-2,8-diazabicyclo[ 4.3.0]nonane are hydrogenated over 1.1 g of palladium on active charcoal (5%) in 90 ml of methanol at 90° C. and 90 bar. The mixture is then filtered, the filtrate is concentrated on a rotary evaporator, and the residue is distilled in vacuo.

Yield: 5.5 g of enantiomerically pure [S,S]-2-methyl-2,8-diazabicyclo[4.3.0]nonane (identification by derivatisation with Mosher's reagent), boiling point: 78°–81° C./14 mbar.

EXAMPLE D cis-2-Oxa-5,8-diazabicyclo[4.3.0]nonane

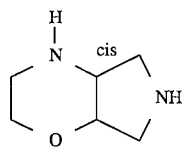

1) trans-1-Benzoyl-3-bromo-4-(2-hydroxyethoxy)-pyrrolidine 95 g (0.55 mol) of 1-benzoyl-3-pyrroline are dissolved in 380 g of ethylene glycol, and 101 g (0.57 mol) of N-bromosuccinimide are added in 5 g portions at room temperature within the space of 2 hours. The solution is subsequently stirred at room temperature overnight, poured into water, extracted with methylene chloride, dried over magnesium sulphate and concentrated. The residue (188 g) was subjected to chromatography on silica gel using ethyl acetate.

Yield: 136.5 g (78% of theory), Content according to GC: 99%.

2) trans-1-Benzoyl-3-bromo-4-(2-tosyloxyethoxy)-pyrrolidine 92 g (0.239 mol) of trans-1-benzoyl-3-bromo-4-(2-hydroxyethoxy)-pyrrolidine, 32 g (0.316 mol) of triethylamine and 1 g of 4-dimethylaminopyridine are dissolved in 750 ml of toluene, and 60 g (0.31 mol) of tosyl chloride in 450 ml of toluene are added dropwise. The mixture is stirred at room temperature for two days, water is added, and the aqueous phase is separated off and extracted with toluene. The toluene solutions are washed with 10% strength hydrochloric acid, dried over magnesium sulphate, concentrated, dissolved in ethyl acetate and filtered through silica gel. The filtrate is concentrated.

Yield: 125 g (91% of theory). The thin layer chromatogram indicates a homogeneous compound.

3) cis-8-Benzoyl-5-benzyl-2-oxa-5,8-diazabicyclo[4.3.0]nonane 124 g (0.265 mol) of trans-1-benzoyl-3-bromo-4-(2-tosyloxyethoxy)-pyrrolidine are heated under reflux overnight in 1.5 l of xylene together with 86 g 0.8 mol) of benzylamine. The salts of the benzylamine are filtered off with suction and the filtrate is concentrated.

Yield of crude product: 91.2 g.

4) cis-5-Benzyl-2-oxa-5,8-diazabicyclo[4.3.0]nonane 91 g (0.265 mol) of cis-8-benzoyl-5-benzyl-2-oxa-5,8-diazabicyclo[4.3.0]nonane are heated under reflux overnight together with 200 ml of concentrated hydrochloric acid and 140 ml of water. After cooling, the benzoic acid is filtered off with suction, the filtrate is concentrated to half the volume, and the solution is made alkaline with potassium carbonate, extracted with chloroform, dried over potassium carbonate, concentrated and distilled.

Yield: 30.7 g (48.8% of theory), Boiling point: 134°–142° C./0.6 mbar, Content according to GC: 92%.

5) cis-2-Oxa-5,8-diazabicyclo[4.3.0]nonane dihydro chloride 26 g (0.11 mol, 92% strength) of cis-5-benzyl-2-oxa-5,8-diazabicyclo[4.3.0]nonane are hydrogenated on 3 g of palladium/active charcoal (10% Pd) at 100° C. and 100 bar $H_2$ in 180 ml of ethanol and 19 ml of concentrated hydrochloric acid. The catalyst is filtered off with suction, the filtrate is concentrated and the crystals which have separated out are dried in a desiccator over phosphorus pentoxide.

Yield: 17.1 g (77% of theory), Melting point: 244°–250° C.

EXAMPLE E

Separation of cis-5-benzyl-2-oxa-5,8-diazabicyclo[ 4.3.0] nonane enantiomers 150.1 g (1 mol) of D(−)-tartaric acid are initially introduced at 60° to 65° C. in 700 ml of methanol, and 218.3 g (1 mol) of cis-5-benzyl-2-oxa-5,8-diazabicyclo[4.3.0] nonane, as a solution in 300 ml of methanol, are added dropwise. The solution is then allowed to cool slowly to about 49° C. until it becomes turbid, and seeding takes place with crystals of 1R,6S-5-benzyl-2-oxa-5,8-diazabicyclo[ 4.3.0]nonane D-tartrate obtained in a prior experiment. The solution is subsequently stirred at this temperature for 30 minutes for the formation of crystal nuclei and is then cooled slowly down to 0° to 3° C. After filtering with suction, the product is washed with a mixture, cooled down to 0° C., of 200 ml of ethanol and 100 ml of methanol and then 3 times with 300 ml of ethanol on each occasion, and subsequently air-dried.

Yield: 160.3 g of 1R,6S-5-benzyl-2-oxa-5,8-diazabicyclo[ 4.3.0]nonane tartrate (87% of theory) Melting point: 174.5° to 176.5° C. ee>97% (after derivatisation with 1-phenyl-ethyl isocyanate and evaluation by HPLC) $[\alpha]_D^{23}$=+24.0° (c=1, methanol)

156.9 g of the 1st batch of crystals are recrystallised from 1,500 ml of methanol.

Yield: 140.0 g (89% recovered) Melting point: 176° to 177° C. $[\alpha]_D^{23}$=+25.2° (c=1, methanol)

The methanolic mother liquor from the 1st crystallisation is concentrated in a rotary evaporator. The syrupy residue (236 g) is dissolved in 500 ml of water, adjusted to pH12 to 13 with 250 ml of 6N sodium hydroxide solution, extracted 3 times with 350 ml of toluene on each occasion, and the extract is dried over sodium carbonate and concentrated in vacuo. The residue, 113.1 g of a brown oil which contains 97% cis-5-benzyl-2-oxa-5,8-diazabicyclo[4.3.0]nonane according to gas chromatographic investigation, is employed without purification for the preparation of the 1S,6R-enantiomer.

113.1 g (0.518 mol) of crude, enriched 1S,6R-5-benzyl-2-oxa- 5,8-diazabicyclo[4.3.0]nonane are dissolved in 155 ml of methanol and added dropwise to a boiling solution of 77.8 g (0.518 mol) of L(+)-tartaric acid in 363 ml of methanol. A crystal slurry forms gradually during the dropwise addition. The mixture is subsequently stirred at 60° C. for 1 hour and then cooled slowly to 0° C. within the space of 2 hours. The crystals are filtered off with suction and washed with a 2:1 mixture, cooled to 0° C., of ethanol and methanol and subsequently 3 times with ethanol. They are then air-dried.

Yield: 145.5 g of 1S,6R-5-benzyl-2-oxa-5,8-diazabicyclo[ 4.3.0]nonane L-tartrate (79% of theory) Melting point: 174.5° to 176.5° C. ee>97% (after derivatisation with 1-phenyl-ethyl isocyanate and evaluation by HPLC) $[\alpha]_D^{23}$= −24.0° (c=1, methanol)

Liberation of the enantiomerically pure bases: 144 g (0.39 mol) of 1S,6R-5-benzyl-2-oxa-5,8-diazabicyclo[ 4.3.0] nonane tartrate are dissolved in 250 ml of water, and 175 ml (1.05 mol) of 6N sodium hydroxide solution are added. The oil which separates out is taken up in 500 ml of toluene, the organic phase is separated off, and the aqueous phase is extracted a further 3 times with 250 ml of toluene on each occasion. The combined organic phases are dried over sodium carbonate, filtered, and concentrated on a rotary evaporator. The residue is distilled under high vacuum through a 20 cm Vigreux column.

Yield: 81.6 g (96% of theory) of 1S,6R-5-benzyl-2-oxa-5,8-diazabicyclo[4.3.0]nonane Boiling point: 120° to 139° C./0.04 to 0.07 mbar Content: 100% determined by gas chromatography Density: δ=1.113 g/ml $[\alpha]_D^{23}$=−60.9° (undiluted) Distillation residue: 0.12 g In a similar way, 76.0 g (93% of theory) of 1R,6S-5-benzyl- 2-oxa-5,8-diazabicyclo[4.3.0]nonane are obtained from 139.2 g (0.376 mol) of 1R,6S-5-benzyl-2-oxa-5,8-diazabicyclo[ 4.3.0]nonane tartrate.

$[\alpha]_D^{23}$=+61.2° (undiluted).

The enantiomer separation described for the cis-5-benzyl-2-oxa-5,8-diazabicyclo[4.3.0]nonane can also be carried out in an analogous manner with trans-5-benzyl-2-oxa-5,8-diazabicyclo[ 4.3.0]nonane to give R,R- and S,S-5-benzyl-2-oxa-5,8-diazabicyclo[4.3.0]nonane.

EXAMPLE F 1) tert-Butyl 3S,4S-4-allyloxy-3-hydroxypyrrolidine-1-carboxylate 16.5 g (0.55 mol) of 80% NaH in 500 ml of absolute dioxane are initially introduced, and a solution of 107.5 g (0.53 mol) of tert-butyl S,S-3,4-dihydroxypyrrolidine-1-carboxylate (DE-A-3 403 194), dissolved in hot absolute dioxane, is added dropwise at 60° C. The mixture is stirred at 60° C. for one hour, and then 64 g (0.53 mol) of allyl bromide are added dropwise. Subsequently, the mixture is stirred at 60° C. for three hours. It is then concentrated and the residue is dissolved in 200 ml of water and 600 ml of methanol. The solution is extracted three times with 200 ml of pentane on each occasion, the methanol is stripped off in a rotary evaporator, and the solution is diluted with 200 ml of water and extracted with methylene chloride. The methylene chloride solution is dried over $MgSO_4$, concentrated, and dissolved in tert-butyl methyl ether (200 ml). 9 g of starting material (44 mmol) crystallised out from this solution overnight. The ether solution is concentrated and distilled.

Yield: 83 g (80% of theory based on recovered starting material and diallyl ether) Boiling point: 149° C./0.7 mbar to 159° C./0.9 mbar.

The distillate contains 5% of the starting material and 4% of the diallyl ether. The pentane extract yielded 17 g of a mixture consisting of 15% of the desired product and 84% of the diallyl ether. $[\alpha]_D^{23}$−10.5° (c=1, methanol)

2) tert-Butyl 3S,4S-3-hydroxy-4-(2-hydroxyethoxy)pyrrolidine-1-carboxylate 64 g (0.24 mol, 91% pure) of tert-butyl 3S,4S-4-allyloxy-3-hydroxypyrrolidine-1-carboxylate are dissolved in 250 ml of methanol, and the solution is then cooled to 0° C. and ozone is passed through it until a downstream washing bottle containing potassium iodide solution, indicates the appearance of ozone and thus completion of the reaction. The remnants of the ozone are removed by a stream of nitrogen, and the resulting ozonide is reduced at 0° C. with 18 g of sodium borohydride, which is added in 1 g portions. Subsequently, the mixture is stirred at room temperature overnight, concentrated, diluted with water, mixed with 20 g of potassium carbonate, and extracted five times with 100 ml of methylene chloride on each occasion. The organic solutions are dried over magnesium sulphate and concentrated.

Yield: 65.8 g (100% of theory). The product is 91% pure by gas chromatography. $[\alpha]_D^{20}=-15.2°$ (c=0.97, methanol).

3) 3S,4S-1-tert-Butoxycarbonyl-3-tosyloxy-4-(2-tosyloxyethoxy)-pyrrolidine 2.7 g (10 mmol, 91% pure) of tert-butyl 3S,4S-3-hydroxy-4-(2-hydroxyethoxy)-pyrrolidine-1-carboxylate are initially introduced in 30 ml of methylene chloride, 6 ml of 45% strength sodium hydroxide 10 solution and 0.1 g of benzyltriethylammonium chloride are added, and a solution of 2.86 g (20 mmol) of tosyl chloride in 10 ml of methylene chloride is then added dropwise while cooling. The mixture is subsequently stirred at room temperature for a further one hour and poured into 20 ml of water, and the organic phase is then separated off and the aqueous phase is extracted with methylene chloride. The organic phases are dried over magnesium sulphate and concentrated.

Yield: 5 g (90% of theory). The product is homogeneous according to thin layer chromatography.

4) tert-Butyl 1S,6R-5-benzyl-2-oxa-5,8-diazabicyclo[4.3.0]nonane-8-carboxylate 87 g (156 mmol) of 3S,4S-1-tert-butoxycarbonyl-3-tosyloxy- 4-(2-tosyloxyethoxy)-pyrrolidine are heated heated under reflux overnight in 1 l of xylene together with 58 g (0.54 mol) of benzylamine. The mixture is cooled, precipitated salts of the benzylamine are filtered off with suction, and the residue is concentrated.

Yield: 43 g (58% of theory). The product is 67% pure by gas chromatography.

5) 1S,6R-5-Benzyl-2-oxa-5,8-diazabicyclo[4.3.0]nonane 43 g (90 mmol) of tert-butyl 1S,6R-5-benzyl-2-oxa-5,8-diazabicyclo[4.3.0]nonane-8-carboxylate are heated under reflux in 35 ml of concentrated hydrochloric acid and 35 ml of water until carbon dioxide evolution ceases. The mixture is made alkaline with potassium carbonate and extracted with chloroform, and the organic solutions are dried over MgSO$_4$, concentrated and distilled twice through a 20 cm Vigreux column.

Yield: 11.1 g (55% of theory) Boiling point: 108°–115° C./0.07 mbar $[\alpha]_D^{26}=-58.3°$ (undiluted).

EXAMPLE G 1) tert-Butyl 3R,4R-4-allyloxy-3-hydroxypyrrolidine-1-carboxylate

The reaction is effected in an analogous manner to Example F1) using tert-butyl R,R-3,4-dihydroxypyrrolidine-1-carboxylate:

Boiling point: 145° C./0.1 mbar $[\alpha]_D^{23}=+9.5°$ (c=1.0, methanol)

The product is 95% pure by gas chromatography.

2) tert-Butyl 3R,4R-3-hydroxy-4-(2-hydroxyethoxy)-pyrrolidine-1-carboxylate

The reaction is effected in an analogous manner to Example F2) using tert-butyl 3R,4R-4-allyloxy-3-hydroxypyrrolidine-1-carboxylate:

Yield: 99% of theory (0.175 molar batch) $[\alpha]_D^{20}=+16.5°$ (c=0.94, methanol)

3) 3R,4R-1-tert-Butoxycarbonyl-3-tosyloxy-4-(2-tosyloxyethoxy)-pyrrolidine

The reaction is effected in an analogous manner to Example F3) using tert-butyl 3R,4R-3-hydroxy-4-(2-hydroxyethoxy)-pyrrolidine-1-carboxylate:

Yield: quantitative (0.11 molar batch).

4) tert-Butyl 1R,6S-5-benzyl-2-oxa-5,8-diazabicyclo[4.3.0]nonane-8-carboxylate

The reaction is effected in an analogous manner to Example F4) using 3R,4R-1-tert-butoxycarbonyl-3-tosyloxy- 4-(2-tosyloxyethoxy)-pyrrolidine:

Yield: 40% of theory (0.1 molar batch).

5) 1R,6S-5-Benzyl-2-oxa-5,8-diazabicyclo[4.3.0]nonane

The reaction is effected in an analogous manner to Example F5) using tert-butyl 1R,6S-5-benzyl-2-oxa-5,8-diazabicyclo[4.3.0]nonane-8-carboxylate:

Yield: 63% of theory (40 mmolar batch) Boiling point: 120° C./0.06 mbar

The product is 95% strength by gas chromatography $[\alpha]_D^{23}=+58.5°$ (undiluted).

EXAMPLE H 1) 1S,6R-2-Oxa-5,8-diazabicyclo[4.3.0]nonane dihydrochloride 7.5 g (34.4 mmol) of 1S,6R-5-benzyl-2-oxa-5,8-diazabicyclo[4.3.0]nonane are hydrogenated on 1 g of palladium-active charcoal (10% Pd) at 100° C. and 100 bar in 200 ml of ethanol with the addition of 7 ml of concentrated hydrochloric acid. The catalyst is filtered off with suction and washed several times with water. The aqueous filtrate is concentrated, as a result of which the residue crystallises. The crystals are triturated thoroughly with ethanol, filtered off with suction and air-dried.

Yield: 4.6 g (66.5% of theory) Melting point: 233°–235° C.

2) 1S,6R-2-Oxa-5,8-diazabicyclo[4.3.0]nonane 59 g (0.27 mol) of 1S,6R-5-benzyl-2-oxa-5,8-diazabicyclo[ 4.3.0] nonane are hydrogenated on 5 g of palladium-active charcoal (10% Pd) at 120° C. and 120 bar in 500 ml of ethanol. The catalyst is filtered off with suction, the filtrate is concentrated and the residue is distilled.

Yield: 32.9 g (95% of theory) Boiling point: 65° C./0.03 mbar Rotation value: $[\alpha]_D^{28}=+8.2°$ (undiluted). ee value: $\geq 99.5\%$ (by derivatisation with Mosher reagent).

EXAMPLE I 1) 1R,6S-2-Oxa-5,8-diazabicyclo[4.3.0]nonane dihydrochloride

The reaction is effected in an analogous manner to Example H1) using 1R,6S-5-benzyl-2-oxa-5,8-diazabicyclo [4.3.0]nonane:

Yield: 77% of theory (23.8 mmolar batch) Melting point: 230°–232° C.

2) 1R,6S-2-Oxa-5,8-diazabicyclo[4.3.0]nonane

The reaction is effected in an analogous manner to Example H2) using 1R,6S-5-benzyl-2-oxa-5,8-diazabicyclo[ 4.3.0]nonane:

Yield: 93.3% of theory (1.58 molar batch) Boiling point: 63°–65° C./0.03 mbar Rotation value: $[\alpha]_D^{23}=-8.4°$ (undiluted) ee value: $\geq 99.5\%$ (by derivatisation with Mosher reagent).

1R,6R- and 1S,6S-2-Oxa-5,8-diazabicyclo[4.3.0]nonane may be obtained in an analogous manner.

EXAMPLE J 1R,6S-2-Oxa-5,8-diazabicyclo[4.3.0]nonane dihydrobromide 1) 1R,6S-5-(1R-Phenylethyl)-8-tosyl-2-oxa-5,8-diazabicyclo[ 4.3.0]nonane 101.8 g (0.196 mol) of trans-3-bromo-1-tosyl-4-(2-tosyloxy-ethoxy)-pyrrolidine and 72 g (0.584 mol) of R-(+)-1-phenylethylamine are heated under reflux overnight in 900 ml of xylene. The cooled solution is washed with 2N sodium hydroxide solution and dried over potassium carbonate, and the drying agent is then removed and the solution concentrated. On cooling, crystals separate out from the residue and were filtered off with suction and recrystallised from a mixture consisting of 750 ml of cleaning benzine and 200 ml of n-butanol.

Yield: 15 g (39.6% of theory of optically pure material) Melting point: 188° C., Rotation value: $[\alpha]_D^{28}=+103.7°$ (c=1, CHCl$_3$).

2) 1R,6S-8-Tosyl-2-oxa-5,8-diazabicyclo[4.3.0]nonane 13 g (33.6 mmol) of 1R,6S-5-(1R-phenylethyl)-8-tosyl-2-oxa-5,8-diazabicyclo[4.3.0]nonane are hydrogenated on 2.5 g of palladium-activated charcoal (10% Pd) at 100° C. and 100 bar in 200 ml of ethanol. The catalyst is filtered off with suction, the is filtrate is concentrated and the residue recrystallised from 30 ml of toluene.

Yield: 7.5 g (79% of theory), Melting point: 160°–161° C., Rotation value: $[\alpha]_D^{23}+17.5°$ (c=1.21, CHCl$_3$).

3) 1R,6S-2-Oxa-5,8-diazabicyclo[4.3.0]nonane dihydrobromide 7 g (24.8 mmol) of 1R,6S-8-tosyl-2-oxa-5,8-diazabicyclo[ 4.3.0]nonane are dissolved in 25 ml of a 33% strength solution of hydrogen bromide in glacial acetic acid, and 5 g of phenol are then added and the mixture is stirred at room temperature overnight. The mixture is diluted with diisopropyl ether and the salt which has crystallised out is filtered off with suction and air-dried.

Yield: 5.5 g.

Derivatisation with Mosher reagent and gas chromatographic analysis indicates only one detectable enantiomer (ee≧99.5% ).

Preparation of the intermediates

EXAMPLE Z1

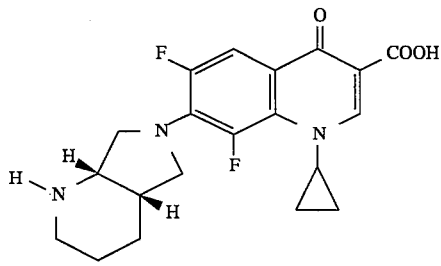

A. 1-Cyclopropyl-7-([S,S]-2,8-diazabicyclo[4.3.0]non-8-yl)-6,8-difluoro-1,4-dihydro-4-oxo-3-quinolinecarboxylic acid 141.5 g (0.5 mol) of 1-cyclopropyl-6,7,8-trifluoro-1,4-dihydro- 4-oxo-3-quinolinecarboxylic acid are heated under reflux for 1 hour in a mixture consisting of 1500 ml of acetonitrile and 750 ml of dimethylformamide in the presence of 55 g (0.5 mol) of 1,4-diazabicyclo[2.2.2]-octane together with 69.25 g (0.55 mol) of (+)-[S,S]-2,8-diazabicyclo[ 4.3.0]nonane (ee 99.5%, GC 99.8% pure). The suspension is cooled and the precipitate is filtered off with suction, washed with water and subsequently stirred with 1 l of water (pH 7). The sediment is filtered off with suction and dried at 60° C. in an air-circulation oven.

Yield: 163.4 g (84% of theory), Melting point: 249°–251° C. (with decomposition).

B. (−)-1-Cyclopropyl-7-([S,S]-2,8-diazabicyclo[4.3.0]non-8-yl)-6,8-difluoro-1,4-dihydro-4-oxo-3-quinolinecarboxylic acid hydrochloride 6.0 g (15.4 mmol) of 1-cyclopropyl-7-([S,S]-2,8-diazabicyclo[ 4.3.0]non-8-yl)-6,8-difluoro-1,4-dihydro-4-oxo-3-quinolinecarboxylic acid are dissolved in 40 ml of half-concentrated hydrochloric acid at 60° C., and the solution of the hydrochloride filtered. The filtrate is concentrated down to half the volume, cooled in ice, and 40 ml of ethanol are added. The yellow crystalline product is filtered off with suction, washed with ethanol and dried at 60° C. under high vacuum, during which the colour becomes lighter. 5.51 g (84% of theory) of the hydrochloride, which is already very pure, are obtained.

For further purification, it is dissolved in 50 ml of hot water. 5 ml of half-concentrated hydrochloric acid are added to the yellow solution, which is then cooled in ice, and the precipitated crystalline product is filtered off with suction, washed well with ethanol, and dried first at room temperature and then at 100° C. under high Vacuum.

Yield: 4.64 g (70.8% of theory), Melting point: 324°–325° C. (with decomposition), TLC (silica gel, dichloromethane/methanol/17% strength aqueous ammonia=30:8:1): homogeneous, $R_f$ value: 0.3, $[\alpha]_D^{25}$: −256° (c=0.5, H$_2$O), Content (HPLC): 99.4% pure,

EXAMPLE Z2

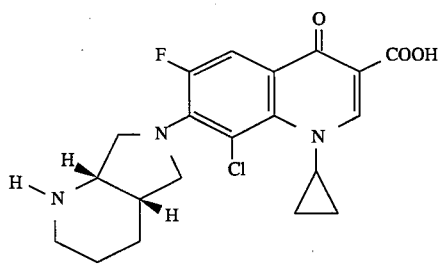

A. 8-Chloro-1-cyclopropyl-7-([S,S]-2,8-diazabicyclo[4.3.0] non-8-yl)-6-fluoro-1,4-dihydro-4-oxo-3-quinolinecarboxylic acid 15 g (50 mmol) of 8-chloro-1-cyclopropyl-6,7-difluoro-1,4-dihydro-4-oxo-3-quinolinecarboxylic acid are heated under reflux for 1 hour in a mixture consisting of 150 ml of acetonitrile/75 ml of dimethylformamide in the presence of 8.25 g (75 mmol) of 1,4-diazabicyclo[2.2.2]octane (DABCO) together with 7.0 g (55 mmol) of (+)-[ S,S]-2,8-diazabicyclo[4.3.0]nonane. The solution is cooled and scratched to induce crystallisation, and the precipitate which has separated out is, after standing overnight, filtered off with suction, washed with acetonitrile and dried at 100° C. in an air-circulation drying oven.

Yield: 13.5 g (66.6% of theory), Melting point: 193°–196° C. (with decomposition), $R_f$ value (silica gel; methylene chloride/methanol/17% strength aqueous $NH_3$=30:8:1): 0.4.

B. 8-Chloro-1-cyclopropyl-7-([S,S]-2,8-diazabicyclo[4.3.0] non-8-yl)-6-fluoro-1,4-dihydro-4-oxo-3-quinolinecarboxylic acid hydrochloride 13.1 g (32 mmol) of 8-chloro-1-cyclopropyl-7-([S,S]-2, 8-diazabicyclo[ 4.3.0]non-8-yl)-6-fluoro-1,4-dihydro-4-oxo- 3-quinolinecarboxylic acid are suspended in 50 ml of water and dissolved by the addition of 50 ml of half-concentrated hydrochloric acid. The solution is filtered through a glass frit and concentrated in vacuo, and the residue is stirred with about 300 ml of absolute ethanol. The suspension is cooled in ice, and the precipitate is filtered off with suction, washed with ethanol and dried firstly at room temperature and then at 100° C. in vacuo.

Yield: 13.4 g (93.8% of theory); Melting point: 328°–330° C. (with decomposition); $R_f$ value (silica gel; methylene chloride/methanol/17% strength aqueous $NH_3$= 30:8:1): 0.4; Content (HPLC): 99.9% pure, $[\alpha]_D^{24}$: −164.4° (c=0.45, $H_2O$).

EXAMPLE Z3

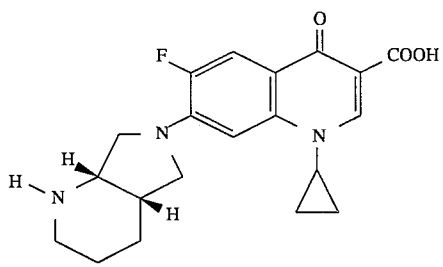

Using 1-cyclopropyl-6,7-difluoro-1,4-dihydro-4-oxo-3-quinolinecarboxylic acid, the following are obtained in an analogous manner to Example Z1:

A. 1-Cyclopropyl-7-([S,S]-2,8-diazabicyclo[4.3.0]non-8-yl)- 6-fluoro-1,4-dihydro-4-oxo-3-quinolinecarboxylic acid, Melting point: 256°–258° C. (with decomposition).

B. 1-Cyclopropyl-7-([S,S]-2,8-diazabicyclo[4.3.0]non-8-yl)- 6-fluoro-1,4-dihydro-4-oxo-3-quinolinecarboxylic acid hydrochloride, Melting point: >320° C. (with decomposition), $[\alpha]_D^{26}$: −90.6° (c=0.48, $H_2O$).

EXAMPLE Z4

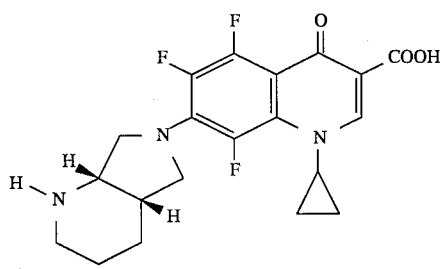

A. 6 g (20 mmol) of 1-cyclopropyl-5,6,7,8-tetrafluoro-1, 4-dihydro-4-oxo-3-quinolinecarboxylic acid are heated under reflux for 1 hour in 40 ml of acetonitrile/ 20 ml of N-methylpyrrolidone in the presence of 2.2 g (20 mmol) of 1,4-diazabicyclo[2.2.2]octane together with 2.7 g (21.4 mmol) of (+)-[S,S]-2,8-diazabicyclo[ 4.3.0]nonane. The resulting suspension is cooled, and the precipitate is filtered off with suction, washed with acetonitrile and dried at 100° C./12 mbar.

Yield: 6.7 g (82.3% of theory) of 1-cyclopropyl-7-([ S,S]-2,8-diazabicyclo[4.3.0]non-8-yl)-5,6,8-trifluoro- 1,4-dihydro-4-oxo-3-quinolinecarboxylic acid, Melting point: 257°–259° C. (with decomposition); after recrystallisation from glycol monomethyl ether: melting point: 260°–265° C. (with decomposition).

B. 1.5 g (3.7 mmol) of the product from step A are introduced into 6 ml of 1N hydrochloric acid. After a short time, the hydrochloride precipitates out and is filtered off with suction, washed twice with 5 ml of ethanol on each occasion, and dried at 100° C./ 12 mbar.

Yield: 1.4 g (85.7% of theory) of 1-cyclopropyl-7-([ S,S]-2,8-diazabicyclo[4.3.0]non-8-yl)-5,6,8-trifluoro- 1,4-dihydro-4-oxo-3-quinolinecarboxylic acid hydrochloride, Melting point: >310° C. (with decomposition), $[\alpha]_D^{26}$: −272° (c=0.5, $H_2O$).

EXAMPLE Z5

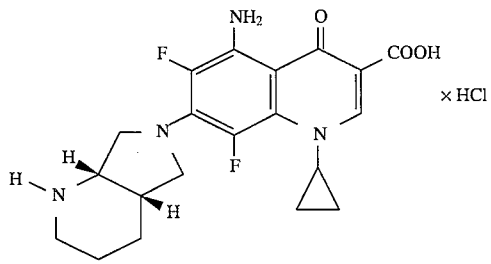

15 ml of liquid ammonia are added to 5.2 g (13 mmol) of the product from Example Z4A in 80 ml of pyridine in an autoclave, and the mixture is heated at 130° C. for 12 hours. Subsequently, the reaction mixture is cooled and the autoclave pressure released, and the mixture is then concentrated and the residue treated with acetonitrile in an ultrasonic bath. The undissolved precipitate is filtered off with suction, the residue is dissolved in about 150 ml of hot water, the solution is filtered, and the hydrochloride is precipitated with 10 ml of half-concentrated hydrochloric acid, filtered off with suction, and dried at 100° C. in an air-circulation drying oven. The resultant product is suspended in 100 ml of glycol monomethyl ether at 110°–115° C. and dissolved by the addition of 38 ml of half-concentrated hydrochloric acid. The solution is filtered hot through a glass frit and cooled, and the yellow crystalline product which has precipitated out is filtered off with suction, washed with ethanol and dried at 120° C./12 mbar.

Yield: 2.5 g (44% of theory) of 5-amino-1-cyclopropyl-7-([ S,S]-2,8-diazabicyclo[4.3.0]non-8-yl)-6,8-difluoro-1,4-dihydro- 4-oxo-3-quinolinecarboxylic acid hydrochloride, Melting point: >335° C. (with decomposition; dark coloration even below 335° C.), $[\alpha]_D^{28}$: −280.8° (c=0.53, $H_2O$).

EXAMPLE Z6

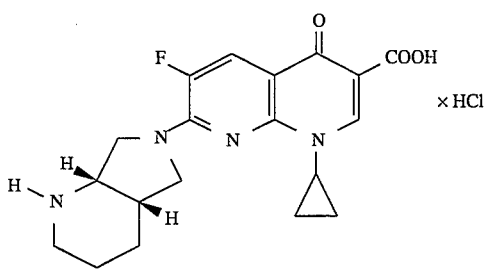

1.4 g (5 mmol) of 7-chloro-1-cyclopropyl-6-fluoro-1,4-dihydro- 4-oxo-1,8-naphthyridine-3-carboxylic acid are stirred in 15 ml of acetonitrile together with 1.3 g (10.3 mmol) of (+)-[S,S]-2,8-diazabicyclo[4.3.0]nonane at room temperature for 1 hour with the exclusion of water. After standing overnight, the mixture is filtered with suction, and the sediment is washed with acetonitrile and, for purification, subjected to chromatography on silica gel (eluent: methylene chloride/methanol/17% strength aqueous ammonia 30:8:1; $R_f$ value: 0.4). The resulting 1-cyclopropyl-7-([S,S]-diazabicyclo[4.3.0]non-8-yl)-6-fluoro-1,4-dihydro-4-oxo-1,8-naphthyridine-3-carboxylic acid is dissolved in 15 ml of half-concentrated hydrochloric acid and the solution is then evaporated and the residue stirred with ethanol. The precipitate is filtered off with suction, washed with ethanol and dried at 120° C./12 mbar.

Yield: 960 mg (47% of theory) of 1-cyclopropyl-7-([S,S]-2,8-diazabicyclo[4.3.0]non-8-yl)-6-fluoro-1,4-dihydro-4-oxo- 1,8-naphthyridine-3-carboxylic acid hydrochloride, Melting point: 345°–346° C. (with decomposition), $[\alpha]_D^{30}$: +5.4° (c=0.5, $H_2O$).

EXAMPLE Z7

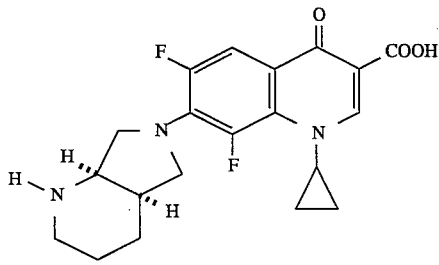

Using (–)-[R,R]-2,8-diazabicyclo[4.3.0]nonane, the following are obtained in an analogous manner to Example Z1:

A. 1-Cyclopropyl-7-([R,R ]-2,8-diazabicyclo[4.3.0]non-8-yl)- 6,8-difluoro-1,4-dihydro-4-oxo-3-quinolinecarboxylic acid, Melting point: 247°–249° C. (with decomposition).

B. 1-Cyclopropyl-7-([R,R]-2,8-diazabicyclo[4.3.0]non-8-yl)- 6,8-difluoro-1,4-dihydro-4-oxo-3-quinolinecarboxylic acid hydrochloride, Melting point: 322°–326° C. (with decomposition), Content (HPLC): 99.4% pure, ee: 98.6%, $[\alpha]_D^{24}$: +250° (c=0.5, $H_2O$).

EXAMPLE Z8

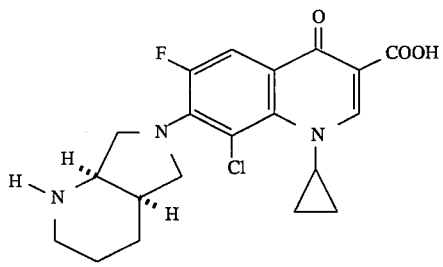

Using (–)-[R,R]-2,8-diazabicyclo[4.3.0]nonane, the following are obtained in an analogous manner to Example Z2:

A. 8-Chloro-1-cyclopropyl-7-[R,R]-2,8-diazabicyclo [4.3.0]non-8-yl)-6-fluoro-1,4-dihydro-4-oxo-3-quinolinecarboxylic acid, Melting point: 192°–195° C. (with decomposition).

B. 8-Chloro-1-cyclopropyl-7-[R,R]-2,8-diazabicyclo [4.3.0]non-8-yl)-6-fluoro-1,4-dihydro-4-oxo-3-quinolinecarboxylic acid hydrochloride, Melting point: 323°–324° C. (with decomposition), Content (HPLC): 99.9% pure, $[\alpha]_D^{24}$: +164.5° (c=0.53, $H_2O$), $C_{20}H_{21}ClFN_3O_3 \cdot HCl$ (442.3) Calculated: C 54.3 H 5.0 N 9.5 Cl 16.0 Found: C 54.2 H 5.0 N 9.5 Cl 16.1

EXAMPLE Z9

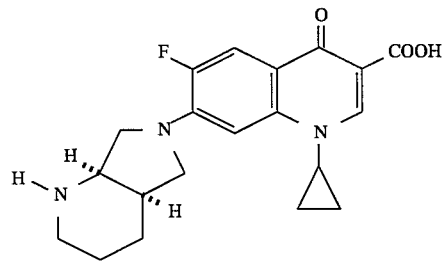

The following are obtained from 1-cyclopropyl-6,7-difluoro- 1,4-dihydro-4-oxo-3-quinolinecarboxylic acid and (–)-[R,R]-2,8-diazabicyclo[4.3.0]nonane in an analogous manner to Example Z1:

A. 1-Cyclopropyl-7-([R,R]-2,8-diazabicyclo[4.3.0]non-8-yl)- 6-fluoro-1,4-dihydro-4-oxo-3-quinolinecarboxylic acid, Melting point: 254°–258° C. (with decomposition).

B. 1-Cyclopropyl-7-([R,R]-2,8-diazabicyclo[4.3.0]non-8-yl)- 6-fluoro-1,4-dihydro-4-oxo-3-quinolinecarboxylic acid hydrochloride, Melting point: decomposition above 320° C., $[\alpha]_D^{24}$: +92.5° (c=0.53, $H_2O$).

EXAMPLE Z10

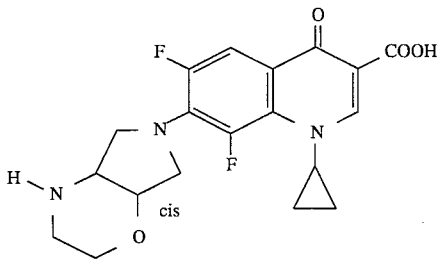

A. 1-Cyclopropyl-6,8-difluoro-1,4-dihydro-7-(cis-2-oxa-5,8-diazabicyclo[4.3.0]non-8-yl)-4-oxo-3-quinolinecarboxylic acid:

1.43 g (5 mmol) of 1-cyclopropyl-6,7,8-trifluoro-1,4-dihydro-4-oxo-3-quinolinecarboxylic acid are heated under reflux for 1 hour with 0.74 g (5.4 mmol) of 93% pure cis-2-oxa-5,8-diazabicyclo[4.3.0]nonane in a mixture consisting of 15 ml of acetonitrile/75 ml of dimethylformamide in the presence of 0.67 g (6 mmol) of 1,4-diazabicyclo[2.2.2]-octane. The suspension is concentrated, the residue is stirred with water, and the precipitate is filtered off with suction and dried at 80° C. in vacuo.

Yield: 1.67 g (85.4% of theory), Melting point: 210°–212° C. (with decomposition).

B. 1-Cyclopropyl-6,8-difluoro-1,4-dihydro-7-(cis-2-oxa-5,8-diazabicyclo[4.3.0]non-8-yl)-4-oxo-3-quinolinecarboxylic acid hydrochloride:

1.6 g (4 mmol) of the product from step A are dissolved at 60° C. in 120 ml of half-concentrated hydrochloric acid, the solution is concentrated, the residue is stirred with ethanol, and the precipitate is filtered off with suction and dried at 90° C. in vacuo.

Yield: 1.57 g, Melting point: 300°–303° C. (with decomposition), Content (HPLC): 97% pure.

C. Using 1R,6S-2-oxa-5,8-diazabicyclo[4.3.0]nonane, 1-cyclopropyl- 6,8-difluoro-1,4-dihydro-7-(1R,6S-2-oxa-5,8-diazabicyclo[4.3.0]non-8-yl)-4-oxo-3-quinolinecarboxylic acid with a melting point of 204°–206° C. (with decomposition) is obtained in an analogous manner to Example Z10A.

D. Using the betaine from Example Z10C, 1-cyclopropyl-6,8-difluoro-1,4-dihydro-7-(1R,6S-2-oxa-5,8-diazabicyclo[4.3.0]non-8-yl)-4-oxo-3-quinolinecarboxylic acid hydrochloride with a melting point of 324°–325° C. (with decomposition) is obtained in an analogous manner to Example Z10B.

$[\alpha]_D^{24}$: −241° (c=0.59, H$_2$O).

E. Using 1S,6R-2-oxa-5,8-diazabicyclo[4.3.0]nonane, 1-cyclopropyl- 6,8-difluoro-1,4-dihydro-7-(1S,6R-2-oxa-5,8-diazabicyclo[4.3.0]non-8-yl)-4-oxo-3-quinolinecarboxylic acid with a melting point of 204°–206° C. (with decomposition) is obtained in an analogous manner to Example Z10A.

$[\alpha]_D^{25}$: +248° (c=0.57, DMF).

F. Using the betaine from Example Z10E, 1-cyclopropyl-6,8-difluoro-1,4-dihydro-7-(1S,6R-2-oxa-5,8-diazabicyclo[4.3.0]non-8-yl)-4-oxo-3-quinolinecarboxylic acid hydrochloride with a melting point of 323° C. (with decomposition) is obtained in an analogous manner to Example Z10B.

$[\alpha]_D^{26}$: +238° (c=0.5, H$_2$O).

EXAMPLE Z11

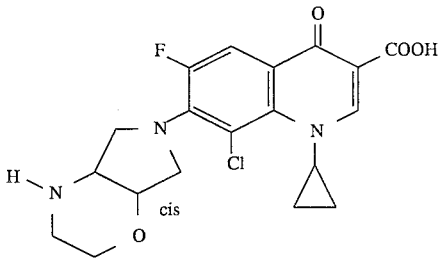

Using 8-chloro-1-cyclopropyl-6,7-difluoro-1,4-dihydro-4-oxo- 3-quinolinecarboxylic acid, the following are obtained in an analogous manner to Example Z10:

A. 8-Chloro-1-cyclopropyl-6-fluoro-1,4-dihydro-7-(cis-2-oxa-5,8-diazabicyclo[4.3.0]non-8-yl)-4-oxo-3-quinolinecarboxylic acid, Melting point: 180°–185° C. (with decomposition).

B. 8-Chloro-1-cyclopropyl-6-fluoro-1,4-dihydro-7-(cis-2-oxa-5,8-diazabicyclo[4.3.0]non-8-yl)-4-oxo-3-quinolinecarboxylic acid hydrochloride, Melting point: 227°–232° C. (with decomposition).

C. 8-Chloro-1-cyclopropyl-6-fluoro-1,4-dihydro-7-(1R,6S-2-oxa-5,8-diazabicyclo[4.3.0]non-8-yl)-4-oxo-3-quinolinecarboxylic acid, Melting point: 186°–188° C. (with decomposition). $[\alpha]_D^{26}$: −269° (c=0.5, DMF).

D. 8-Chloro-1-cyclopropyl-6-fluoro-1,4-dihydro-7-(1R,6S-2-oxa-5,8-diazabicyclo[4.3.0]non-8-yl)-4-oxo-3-quinolinecarboxylic acid hydrochloride, Melting point: 278°–280° C. (with decomposition). $[\alpha]_D^{24}$: −208° (c=0.5, H$_2$O).

E. 8-Chloro-1-cyclopropyl-6-fluoro-1,4-dihydro-7-(1S,6R-2-oxa-5,8-diazabicyclo[4.3.0]non-8-yl)-4-oxo-3-quinolinecarboxylic acid, Melting-point: 188°–190° C. (with decomposition). $[\alpha]_D^{25}$: +270° (c=0.5, DMF).

F. 8-Chloro-1-cyclopropyl-6-fluoro-1,4-dihydro-7-(1S,6R-2-oxa-5,8-diazabicyclo[4.3.0]non-8-yl)-4-oxo-3-quinolinecarboxylic acid hydrochloride, Melting point: 292°–294° C. (with decomposition). $[\alpha]_D^{27}$: +193° (c=0.5, H$_2$O).

EXAMPLE Z12

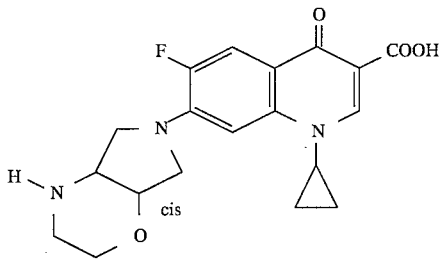

Using 1-cyclopropyl-6,7-difluoro-1,4-dihydro-4-oxo-3-quinolinecarboxylic acid, the following are obtained in an analogous manner to Example Z10A:

A. 1-Cyclopropyl-6-fluoro-1,4-dihydro-7-(cis-2-oxa-5,8-diazabicyclo[4.3.0]non-8-yl)-4-oxo-3-quinolinecarboxylic acid, Melting point: 246°–249° C. (with decomposition) (from glycol monomethyl ether).

B. 1-Cyclopropyl-6-fluoro-1,4-dihydro-7-(1R,6S-2-oxa-5,8-diazabicyclo[4.3.0]non-8-y)-4-oxo-3-quinolinecarboxylic acid, Melting point: 243°–245° C. (with decomposition).

C. 1-Cyclopropyl-6-fluoro-1,4-dihydro-7-(1R,6S-2-oxa-5,8-diazabicyclo[4.3.0]non-8-yl)-4-oxo-3-quinolinecarboxylic acid hydrochloride, Melting point: 300° C. (decomposition) $[\alpha]_D^{23}$: –99° (c=0.5, H$_2$O).

EXAMPLE Z13

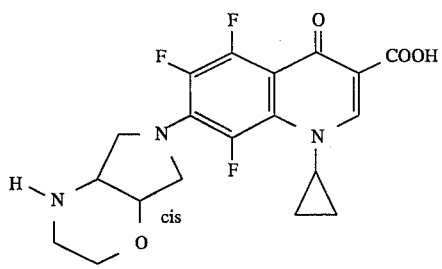

Using 1-cyclopropyl-5,6,7,8-tetrafluoro-1,4-dihydro-4-oxo-3-quinolinecarboxylic acid, the following are obtained in an analogous manner to Example Z10A:

A. 1-Cyclopropyl-5,6,8-trifluoro-1,4-dihydro-7-(cis-2-oxa-5,8-diazabicyclo[4.3.0]non-8-yl)-4-oxo-3-quinolinecarboxylic acid, Melting point: 210°–216° C. (with decomposition).

B. 1-Cyclopropyl-5,6,8-trifluoro-1,4-dihydro-7-(1R,6S-2-oxa-5,8-diazabicyclo[4.3.0]non-8-yl)-4-oxo-3-quinolinecarboxylic acid, Melting point: 234°–237° C. (with decomposition). $[\alpha]_D^{24}$: –287° (c=0.5, DMF).

C. 1-Cyclopropyl-5,6,8-trifluoro-1,4-dihydro-7-(1S,6R-2-oxa-5,8-diazabicyclo[4.3.0]non-8-yl)-4-oxo-3-quinolinecarboxylic acid, Melting point: 236°–237° C. (with decomposition). $[\alpha]_D^{24}$: +282° (c=0.5, DMF).

EXAMPLE Z14

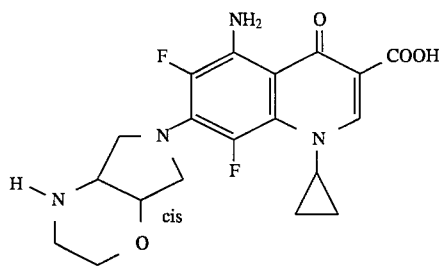

A. 5 ml of liquid ammonia are added to 4.1 g (10 mmol) of the product from Example Z13A in 40 ml of pyridine and the mixture is heated at 130° C. for 10 hours in an autoclave. After cooling, the precipitate is filtered off with suction, washed with water and dried at 100° C. in an air-circulation drying oven. The crude product (2 g) is purified by recrystallisation from glycol monomethyl ether: yellow crystalline product.

Yield: 1.3 g (31% of theory) of 5-amino-1-cyclopropyl-6,8-difluoro-1,4-dihydro-7-(cis-2-oxa-5,8-diazabicyclo[4.3.0]non-8-yl)-4-oxo-3-quinolinecarboxylic acid, Melting point: 233°–240° C. (with decomposition).

B. Using the product from Example Z13C, 5-amino-1-cyclopropyl- 6,8-difluoro-1,4-dihydro-7-(1R,6S-2-oxa-5,8-diazabicyclo[4.3.0]non-8-yl)-4-oxo-3-quinolinecarboxylic acid is obtained in an analogous manner, Melting point: 212°–214° C. (with decomposition), $[\alpha]_D^{25}$: –260° (c=0.5, DMF).

C. Using the product from Example Z13C, 5-amino-1-cyclopropyl- 6,8-difluoro-1,4-dihydro-7-(1S,6R-2-oxa- 5,8-diazabicyclo[4.3.0]non-8-yl)-4-oxo-3-quinolinecarboxylic acid is obtained in an analogous manner, Melting point: 213°–215° C. (with decomposition), $[\alpha]_D^{26}$: +261° (c=0.5, DMF), Mass spectrum: m/e 406 (M$^+$, 95%), 346, 249, 98, 41, 28 (100%).

EXAMPLE Z15

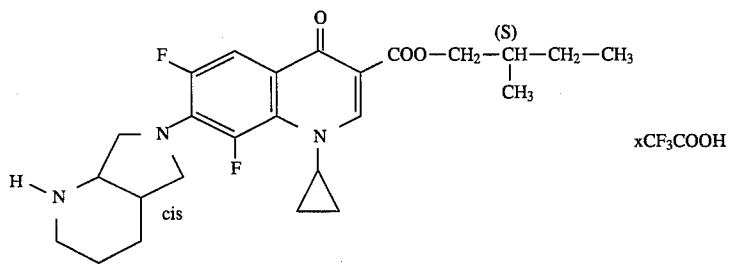

A. 7-(2-tert-Butoxycarbonyl-2,8-diazabicyclo[4.3.0]non-8-yl)-1-cyclopropyl-6,8-difluoro-1,4-dihydro-4-oxo-3-quinolinecarboxylic acid 7.8 g (20 mmol) of 1-cyclopropyl-7-(2,8-diazabicyclo[4.3.0]non-8-yl)-6,8-difluoro-1,4-dihydro-4-oxo- 3-quinolinecarboxylic acid are dissolved in a mixture consisting of 60 ml of dioxane/water (2:1) and 20 ml of 1N sodium hydroxide solution and, while cooling with ice and stirring, 5.24 g (24 mmol) of di-tert-butyl pyrocarbonate are added. The mixture is subsequently stirred at room temperature for 1 hour and allowed to stand overnight. The precipitate which has separated out is filtered off with suction, washed with 250 ml of water, and dried at 50° C. overnight in an air-circulation drying oven.

Yield: 9.34 g (95.5% of theory), Melting point: 216°–219° C. (with decomposition).

B. 2S-Methyl-1-butyl 7-(2-tert-butoxycarbonyl-2,8-diazabicyclo[ 4.3.0]non-8-yl)-1-cyclopropyl-6,8-difluoro- 1,4-dihydro-4-oxo-3-quinolinecarboxylate 2.15 g (4.4 mmol) of the product from step A are suspended in 60 ml of tetrahydrofuran/water (1:1) at room temperature, and 1.65 g (5 mmol) of caesium carbonate are added. The mixture is left to react in an ultrasonic bath at about 40° C. for 20 minutes and then about 40 ml of the solvent are distilled off at 40° C./12 mbar and the remaining solution is lyophilised, with the readily soluble crude caesium salt being obtained. 3.3 g of this crude salt are dissolved in 40 ml of dimethylformamide, 1.4 g of S(+)-1-bromo-2-methylbutane are added, and reaction is carried out in an ultrasonic bath at 40°–50° C. overnight. The resultant suspension is concentrated and the residue is mixed with water and extracted with methylene chloride. After drying with sodium sulphate, the solution is concentrated and the residue is purified by chromatography (silica gel, eluent: methylene chloride/methanol 95:5).

Yield: 950 mg (38% of theory), Melting point: 72°–83° C. (with decomposition).

C. 2S-Methyl-1-butyl 1-cyclopropyl-7-(2,8-diazabicyclo[4.3.0]non-8-yl)-6,8-difluoro-1,4-dihydro-4-oxo- 3-quinolinecarboxylate trifluoroacetate 570 mg (1 mmol) of the product from step B are dissolved in 3 ml of trifluoroacetic acid at room temperature and the solution is concentrated at 60° C./12 mbar. The viscous oil which is obtained is stirred with 5 ml of ether, resulting in a solid product. This is filtered off with suction, washed with ether and dried at 80° C. under high vacuum.

Yield: 450 mg (78% of theory), Melting point: 214°–216° C. (with decomposition), $[\alpha]_D^{25}$: +2.8° (c=0.5, DMF).

EXAMPLE Z16

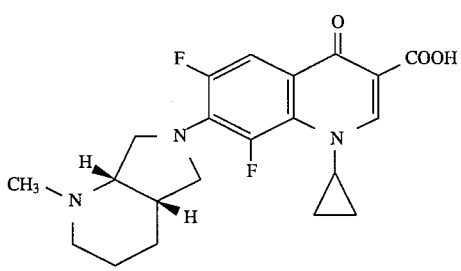

Using [S,S]-2-methyl-2,8-diazabicyclo[4.3.0]nonane, the following are obtained in an analogous manner to Example Z1:

A. 1-Cyclopropyl-6,8-difluoro-1,4-dihydro-7-([S,S]-2-methyl- 2,8-diazabicyclo[4.3.0]non-8-yl)-4-oxo-3-quinolinecarboxylic acid, Melting point: 230°–233° C. (with decomposition) (recrystallised from glycol monomethyl ether);

B. 1-Cyclopropyl-6,8-difluoro-1,4-dihydro-7-([S,S]-2-methyl- 2,8-diazabicyclo[4.3.0]non-8-yl)-4-oxo-3-quinolinecarboxylic acid hydrochloride, Melting point: 258°–260° C. (with decomposition), $[\alpha]_D^{25}$: –216.3° (c=1, H$_2$O).

EXAMPLE Z17

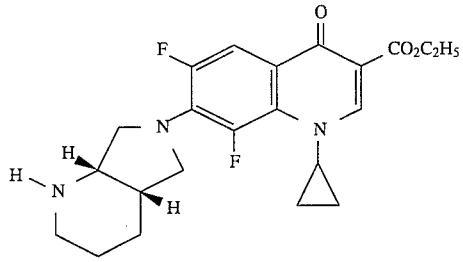

1.52 g (5 mmol) of ethyl 1-cyclopropyl-6,7,8-trifluoro-1, 4-dihydro-4-oxo-3-quinolinecarboxylate are reacted in 30 ml of acetonitrile with 550 mg (5 mmol) of 1,4-diazabicyclo [2.2.2]octane and 760 mg (6 mmol) of (+)-[S,S]-2,8-diazabicyclo[4.3.0]nonane at 50° C. for 2 hours and at 60° C. for 2 hours. After cooling, the suspension which is obtained is filtered with suction, and the precipitate is washed with water and dried at 90° C. in vacuo.

Yield: 0.99 g (47.5% of theory) of ethyl 1-cyclopropyl-7-([S,S]-2,8-diazabicyclo[4.3.0]non-8-yl)-6,8-difluoro-1,4-dihydro- 4-oxo-3-quinolinecarboxylate, Melting point: 194°–195° C. (from acetonitrile), $[\alpha]_D^{23}$: –188.9° (c=0.51, CHCl$_3$).

EXAMPLE Z18

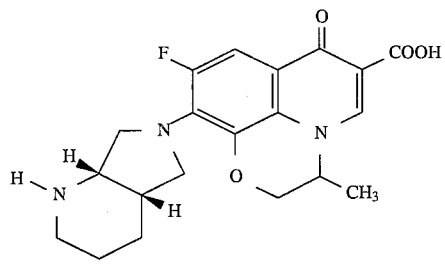

1.4 g (5 mmol) of 9,10-difluoro-2,3-dihydro-3-methyl-7-oxo- 7H-pyrido[1,2,3-de][1,4]-benzoxazine-6-carboxylic acid are reacted in 15 ml of acetonitrile/7.5 ml of dimethylformamide with 0.85 g (7.7 mmol) of 1,4-diazabicyclo[ 2.2.2]octane and 0.7 g (5.6 mmol) of (+)-[S,S]-2,8-diazabicyclo[ 4.3.0]nonane in an analogous manner to EXAMPLE Z1A.

Yield: 1.24 g (64% of theory) of 10-([S,S]-2,8-diazabicyclo[ 4.3.0]non-8-yl)-9-fluoro-2,3-dihydro-3-methyl-7-oxo- 7H-pyrido[1,2,3-de][1,4]benzoxazine-6-carboxylic acid, Melting point: 265°–268° C. (with decomposition), $[\alpha]_D$: –232.2° (c=0.58, CHCl$_3$).

3S-10-([S,S]-2,8-Diazabicyclo[4.3.0]non-8-yl)-9-fluoro-2,3-dihydro-3-methyl-7-oxo-7H-pyrido[1,2,3-de][1,4]benzoxazine- 6-carboxylic acid is also obtained in an analogous manner.

EXAMPLE Z19

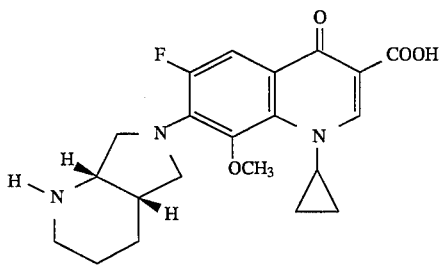

1-Cyclopropyl-6,7-difluoro-1,4-dihydro-8-methoxy-4-oxo-3-quinolinecarboxylic acid is reacted in an analogous manner to Example Z1A and the reaction product is purified by chromatography (silica gel, eluent: methylene chloride/ methanol/ 17% strength aqueous ammonia=30:8:1).

1-Cyclopropyl-7-([S,S]-2,8-diazabicyclo[4.3.0]non-8-yl)-6-fluoro-1,4-dihydro-8-methoxy-4-oxo-3-quinolinecarboxylic acid with a melting point of 203°–208° C. (with decomposition) is obtained.

$[\alpha]_D^{23}$: −193° (c=0.4, CHCl$_3$)

EXAMPLE Z20

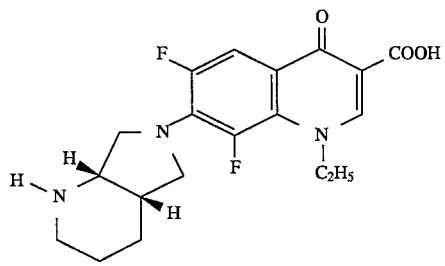

In an analogous manner to Example Z1A, reaction takes place with 1-ethyl-6,7,8-trifluoro-1,4-dihydro-4-oxo-3-quinolinecarboxylic acid, and 1-ethyl-7-([S,S]-2,8-diazabicyclo[4.3.0]-non-8-yl)-6,8-difluoro-1,4-dihydro-4-oxo-3-quinolinecarboxylic acid is obtained with a melting point of 236°–239° C. (with decomposition) (recrystallised from glycol monomethyl ether);

$[\alpha]_D^{23}$: −186.3° (c=0.3, CHCl$_3$).

EXAMPLE Z21

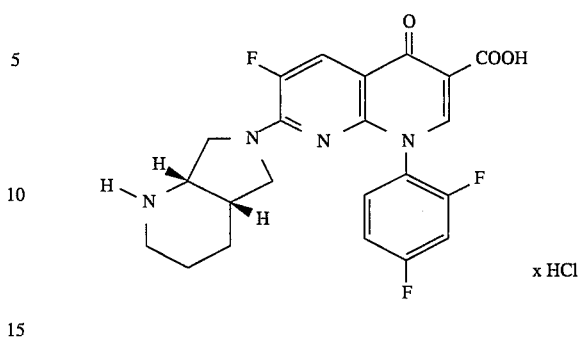

A. Ethyl 7-([S,S]-2,8-diazabicyclo[4.3.0]non-8-yl)-1-(2, 4-difluorophenyl)-6-fluoro-1,4-dihydro-4-oxo-1,8-naphthyridine- 3-carboxylate 1.9 g (5 mmol) of ethyl 7-chloro-1-(2,4-difluorophenyl)-6-fluoro-1,4-dihydro-4-oxo-1,8-naphthyridine- 3-carboxylate are stirred with 680 mg (5.4 mmol) of [S,S]-2,8-diazabicyclo[4.3.0]nonane at 10° C. for 3 hours in 20 ml of acetonitrile and in the presence of 560 mg (5 mmol) of 1,4-diazabicyclo[2.2.2]octane. The suspension is filtered with suction, washed with water and dried. 0.35 g of product is obtained. By concentrating the mother liquors, stirring the residue with water, isolating the undissolved product and purifying by chromatography (silica gel, eluent: dichloromethane/methanol/ 17% strength aqueous ammonia), a further 0.7 g of product is isolated.

Total yield: 1.05 g (44% of theory), Melting point: 184°–185° C. (with decomposition), $[\alpha]_D^{23}$: +6.8° (c=0.46, CHCl$_3$)

B. 7-([S,S]-2,8-Diazabicyclo[4.3.0]non-8-yl)-1-(2,4-difluorophenyl)- 6-fluoro-1,4-dihydro-4-oxo-1,8-naphthyridine- 3-carboxylic acid hydrochloride 0.8 g (1.7 mmol) of the product from step A is heated under reflux for 4 hours in a mixture consisting of 10 ml of acetic acid and 8 ml of half-concentrated hydrochloric acid. The mixture is concentrated, the residue is stirred with a little water, and the precipitate is filtered off with suction, washed with ice-cold ethanol and dried.

Yield: 0.67 g (83% of theory), Melting point: 324°–326° C. (with decomposition), $[\alpha]_D^{25}$: +10.8° (c=0.37, DMF).

EXAMPLE Z22

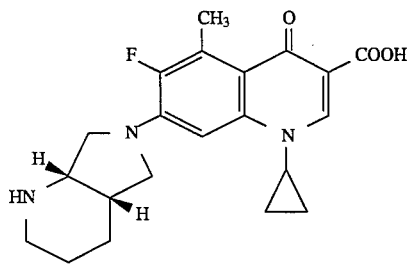

0.56 g (2 mmol) of 1-cyclopropyl-6,7-difluoro-1,4-dihydro- 5-methyl-4-oxo-3-quinolinecarboxylic acid is heated at 120° C. for 2 hours with 0.38 g (3 mmol) of [S,S]-2,8-diazabicyclo[4.3.0]nonane and 0.45 g (4 mmol) of 1,4-diazabicyclo[2.2.2]octane in 3.5 ml of dimethyl sulphoxide. After cooling, the solvent is removed under high vacuum. The residue is taken up with acetonitrile. The solid is separated off, washed with acetonitrile and dried at 60° to 80° C.

Yield: 0.5 g (65% of theory) of 1-cyclopropyl-7-([S,S]-2,8-diazabicyclo[4.3.0]non-8-yl)-6-fluoro-1,4-dihydro-5-methyl- 4-oxo-3-quinolinecarboxylic acid, Melting point: 217°–219° C. (with decomposition), $[\alpha]_D$: −119° (c=0.5, DMF).

EXAMPLE Z23

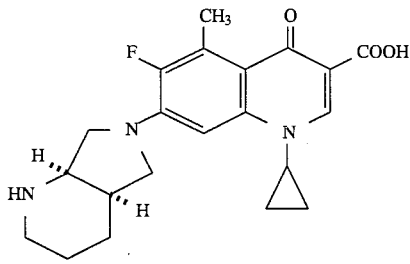

A. 837 mg (3 mmol) of 1-cyclopropyl-6,7-difluoro-1,4-dihydro- 5-methyl-4-oxo-3-quinolinecarboxylic acid are heated under reflux for 2 hours with 1.1 g (10 mmol) of 1,4-diazabicyclo[2.2.2]octane and 665 mg (3.3 mmol) of 1R,6S-2-oxa-5,8-diazabicyclo[4.3.0]nonane dihydrochloride in a mixture consisting of 10 ml of acetonitrile and 5 ml of dimethylformamide. The mixture is evaporated, the residue is stirred with 30 ml of water, and the precipitate is filtered off with suction and dried at 80° C. in vacuo.

Yield: 400 mg (34% of theory) of 1-cyclopropyl-6-fluoro-1,4-dihydro-5-methyl-7-(1R,6S-2-oxa-5,8-diazabicyclo[ 4.3.0]non-8-yl)-4-oxo-3-quinolinecarboxylic acid, Melting point: 213°–214° C. (with decomposition).

B. 0.4 g of the betaine from step A is dissolved in 5 ml of half-concentrated hydrochloric acid at room temperature, and the solution is concentrated and the residue stirred with about 3 ml of ethanol. The precipitate is filtered off with suction and dried at 80° C./12 mbar.

Yield: 290 mg (66% of theory) of 1-cyclopropyl-6-fluoro-1,4-dihydro-5-methyl-7-(1R,6S-2-oxa-5,8-diazabicyclo[ 4.3.0]non-8-yl)-4-oxo-3-quinolinecarboxylic acid hydrochloride, Melting point: 305°–308° C. (with decomposition), $[\alpha]_D^{23}$: −79° (c=0.52, $H_2O$).

EXAMPLE Z24

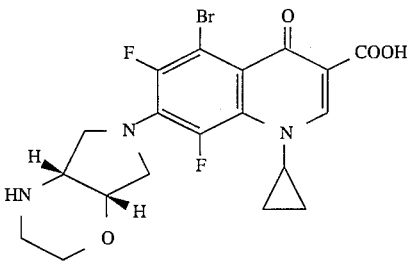

32 mg (1 mmol) of 5-bromo-1-cyclopropyl-6,7,8-trifluoro-1,4-dihydro-4-oxo-3-quinolinecarboxylic acid are heated under reflux for 1.5 hours with 220 mg (2 mmol) of 1,4-diazabicyclo[ 2.2.2]octane and 220 mg (1.1 mmol) of 1S,6R-2-oxa-5,8-diazabicyclo[4.3.0]nonane dihydrochloride in a mixture consisting of 3 ml of acetonitrile and 1.5 ml of dimethylformamide. The suspension is cooled, and the precipitate is filtered off with suction, stirred with 30 ml of water and dried at 90° C. under high vacuum.

Yield: 320 mg (68% of theory) of 5-bromo-1-cyclopropyl-6,8-difluoro-1,4-dihydro-7-(1S,6R-2-oxa-5,8-diazabicyclo[4.3.0]non-8-yl)-4-oxo-3-quinolinecarboxylic acid, Melting point: 263°–264° C. (with decomposition), $[\alpha]_D^{30}$: +251° (c=0.3, $CH_2C_2$).

Preparation of the active compounds

EXAMPLE 1

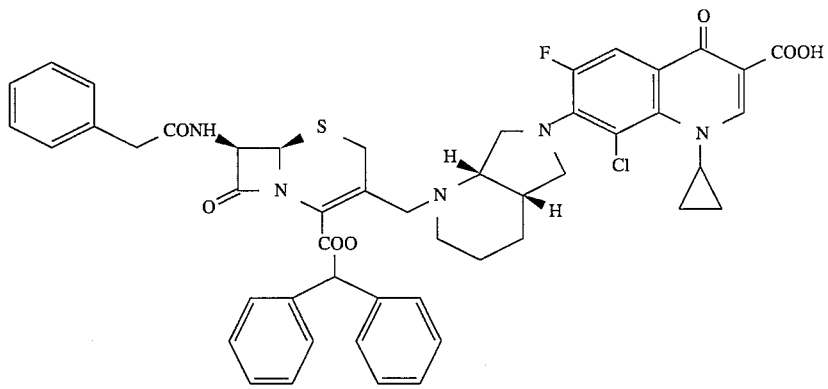

7-[2-([6R,7R]-2-Benzhydryloxycarbonyl-8-oxo-7-phenylacetylamino- 5-thia-1-azabicyclo[4.2.0]oct-2-en-3-yl-methyl)-[ 1S,6S]-2,8-diazabicyclo[4.3.0]non-8-yl]-8-chloro- 1-cyclopropyl-6-fluoro-1,4-dihydro-4-oxo-3-quinolinecarboxylic acid Under an $N_2$ atmosphere, 160 mg (0.4 mmol) of 8-chloro-1-cyclopropyl- 7-[(1S,6S)-2,8-diazabicyclo[4.3.0]non-8-yl]- 6-fluoro-1,4-dihydro-4-oxo-3-quinolinecarboxylic acid are suspended in 2.25 ml of dichloromethane. 283 μl (1.6 mmol) of trimethylsilyltrifluoroacetamide are added and the mixture is stirred at room temperature for 20 minutes; 0.5 g of 3 Å molecular sieves is then added, and the mixture is stirred at room temperature for one hour, and the solution is evaporated to dryness. Subsequently, a solution of 151 mg (0.283 mmol) of benzhydryl [6R,7R]-3-chloromethyl-8-oxo-7-phenylacetylamino-5-thia-1-aza-bicyclo[4.2.0]oct-2-ene-2-carboxylate in 2.25 ml of acetone is added. After addition of 46.6 mg (0.367 mmol) of NaI, the mixture is stirred overnight (20 hours), poured into water, adjusted to pH=4 with 1N HCl, and extracted 3× with ethyl acetate. The organic phase is washed with water, dried over $MgSO_4$ and evaporated to dryness. 96 mg (0.106 mmol) (38% of theory) of the title product are obtained by chromatography on silica gel using $CH_2Cl_2/CH_3OH$ (30:1).

NMR ($CDCl_3$): δ=14.65 (1H), 8.85 (1H), 7.9 (1H), 7.45–7.15 (15H), 6.9 (1H), 6.2 (1H), 5.72 (1H), 4.9 (1H), 4.25 (1H), 4.0–2.1 (10H), 3.7 (1H), 3.4 (1H), 3.7 (2H), 1.9–1.5 (4H), 1.2 (2H) and 0.9 ppm (2H).

In the same way, 1.62 g (3.60 mmol) of 8-chloro-1-cyclopropyl- 7-[(1S,6S)-2,8-diazabicyclo[4.3.0]non-8-yl]-6-fluoro- 1,4-dihydro-4-oxo-3-quinolinecarboxylic acid are reacted to give the title product in 40% yield.

Amorphous powder, decomposition point from 149° C. $R_f$=0.12 (dichloromethane:methanol 97:3) IR(KBr) ν=3412, 2922, 1780, (CO β-lactam), 1728, 1616, 1496, 1436, 1314, 1220, 1177, 1100, 696 $cm^{-1}$ MS(FAB) m/z=902 $(M+H)^+$ 1H-NMR (250 MHz, DMSO-$d_6$) δ=0.94 (m, 2H, cyclopropyl-H), 1.19 (m, 2H, cyclopropyl-H), 1.3–1.7 (m, 4H, —$CH_2$—), 2.0 (m, 1H), 2.4 (m, 1H), 2.90 (m, 1H), 3.15–3.85 (m, 12H, $SCH_2$, $PhCH_2CO$, $CH_2N$, CHN), 4.36 (m, 1H, cyclopropyl-H), 5.17 (d, J=5 Hz, 1H, H-6'), 5.20 (dd, J=8, 5 Hz, 1H, H-7'), 6.95 (s, 1H $CHPh_2$), 7.2–7.5 (m, 15H, Ph), 7.85 (d, J=15 Hz, 1H, CH=CF), 8.80 (s, 1H, NCH=C), 9.08 (d, J=8 Hz, 1H, CONH), 14.82 (s, 1H, COOH).

EXAMPLE 2

7-[2-([6R,7R]-2-Carboxy-8-oxo-7-phenyl acetyl amino-5-thia-1-aza-bicyclo[4.2.0]oct-2-en-3-ylmethyl)-[1S,6S]-2,8-diazabicyclo[4.3.0]non-8-yl]-8-chloro-1-cyclopropyl-6-fluoro- 1,4-dihydro-4-oxo-3-quinolinecarboxylic acid 96 mg of the product from Example 1 are dissolved in 1 ml of dichloromethane, and 1 ml of trifluoroacetic acid and 10 μl of anisole are added and the mixture is stirred at room temperature for one hour. It is evaporated to dryness in vacuo, the residue is stirred in about 1 ml of ethyl acetate/water 1:1, and the mixture is adjusted to pH=4 and filtered with suction. In this way, 10 mg (13% of theory) of the title product are obtained.

NMR ($CF_3COOD$) δ=9.53 (1H), 8.22 (1H), 7.5–7.2 (5H), 5.72 (1H), 5.22 (1H), 5.03–4.5 (5H), 4.17 (1H), 3.9 (3H), 3.7 (2H), 3.45–3.1 (3H), 2.3–2.1 (4H) and 1.8–1.1 ppm (4H).

A further 10 mg of the product can be obtained from the filtered solution by chromatography on silica gel.

EXAMPLE 3

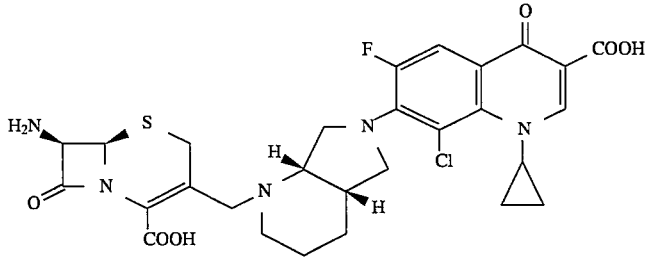

7-[2-(7-Amino-2-carboxy-8-oxo-5-thia-1-aza-bicyclo[4.2.0]oct-2-en-3-ylmethyl)-[1S,6S]-2,8-diazabicyclo[4.3.0]non-8-yl]-8-chloro-1-cyclopropyl-6-fluoro-1,4-dihydro- 4-oxo-3-quinolinecarboxylic acid 10 mg (0.0136 mmol) of the product from Example 2 are stirred in 1 ml of water together with 25 mg of penicillin acylase resin at pH=8.0 (autotitrator) at room temperature for 4 hours. The mixture is filtered and lyophilised. Chromatography next takes place on HP-20 resin using water and water/acetone 4:1. Yield 5.6 mg (67% of theory).

EXAMPLE 4

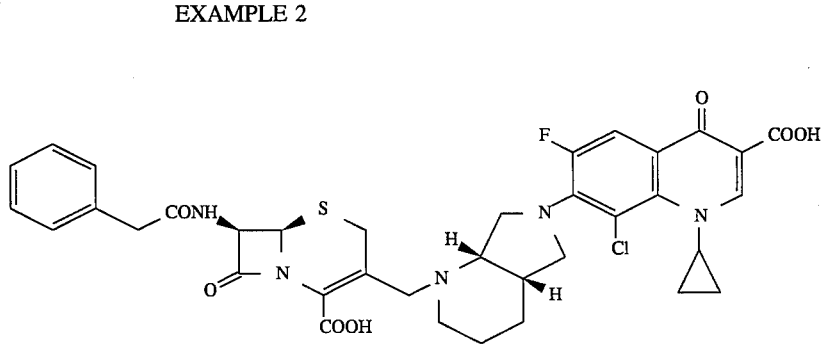

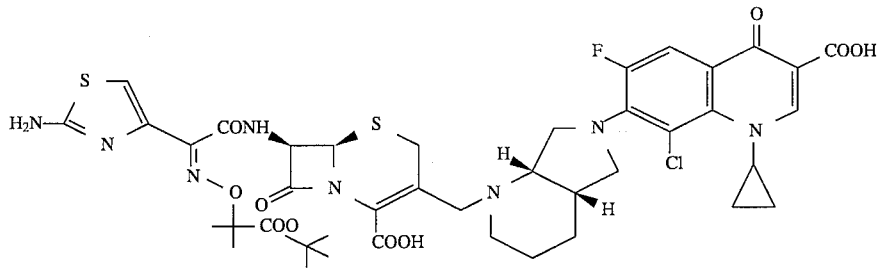

7-[2-([6R,7R]-7-[2-(Amino-thiazol-4-yl)-2-(1-tert-butoxycarbonyl- 1-methyl-ethoxyimino)-acetylamino]-2-carboxy-8-oxo- 5-thia-1-aza-bicyclo[4.2.0]oct-2-en-3-ylmethyl)-[1S,6S]-2,8-diazabicyclo[4.3.0]non-8-yl]-8-chloro-1-cyclopropyl- 6-fluoro-1,4-dihydro-4-oxo-3-quinolinecarboxylic acid A mixture of 62 mg (0.1 mmol) of the product from Example 3, 1.5 ml of tetrahydrofuran, 3 mg of sodium bicarbonate and 1.5 ml of water was stirred at 5° C. for 20 minutes. A solution of 78 mg (0.164 mmol) of 1,1-dimethylethyl (Z)-2-[[[1-(2-amino-4-thiazolyl)-2-benzothiazol-2-ylthio)-2-oxoethyl] imino]oxy]-2-methylpropionate in 1 ml of THF was added, and the mixture was stirred at 5° C. for a further 15 minutes. Stirring took place overnight without a cold bath. After stripping off the tetrahydrofuran in vacuo, the remaining aqueous solution was washed with ethyl acetate, adjusted to pH=5 with 1 N HCl, and the precipitate which had separated out was filtered off with suction, washed with water and a little ethyl acetate, and dried in vacuo, yield 51 mg (55%).

EXAMPLE 5

50 mg (0.054 mmol) of the product from Example 4 were stirred at 5° C. overnight with 2 ml of trifluoroacetic acid, 2 ml of methylene chloride and 0.2 ml of anisole. The mixture is concentrated to dryness, and the residue is treated with ether, yielding the trifluoroacetic acid salt in solid form. Subsequently, the pH is adjusted to 7 in aqueous sodium bicarbonate, and chromatography takes place on a reversed phase column using water and water/acetonitrile 4:1. Yield after lyophilisation: 28 mg (0.031 mmol)=57% of theory.

EXAMPLE 6

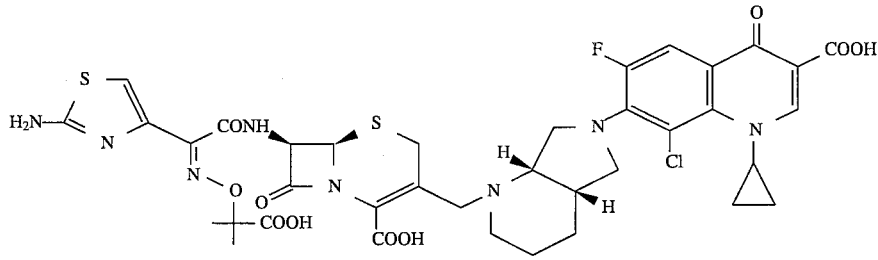

7-[2-([6R,7R]-7-[2-(2-Amino-thiazol-4-yl)-2-(1-carboxy- 1-methyl-ethoxyimino)-acetylamino] -2-carboxy-8-oxo-5-thia-1-aza-bicyclo[4.2.0]oct-2-en-3-ylmethyl)-[1S, 6S]-2,8-diazabicyclo[ 4.3.0]non-8-yl]-8-chloro-1-cyclopropyl-6-fluoro- 1,4-dihydro-4-oxo-3-quinolinecarboxylic acid

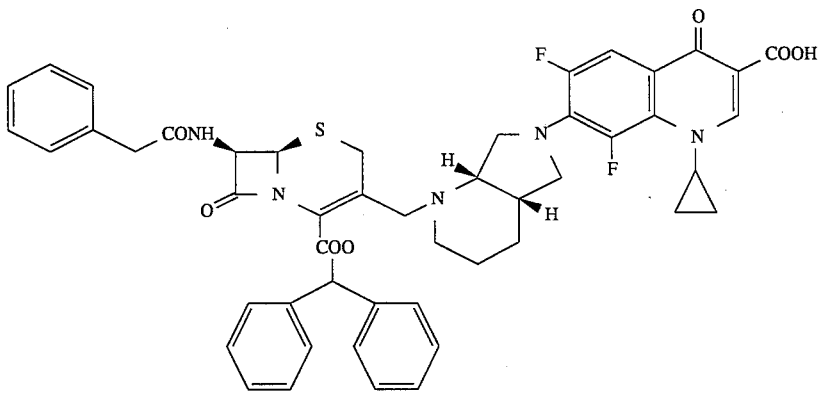

7-[2-([6R,7R]-2-Benzhydryloxycarbonyl-8-oxo-7-phenylacetylamino- 5-thia-1-aza-bicyclo[4.2.0]oct-2-en-3-ylmethyl)-[ 1S,6S]-2,8-diazabicyclo[4.3.0]non-8-yl]-1-cyclopropyl- 6,8-difluoro-1,4-dihydro-4-oxo-3-quinolinecarboxylic acid

In the manner described in Example 1, 150 mg (0.4 mmol) of 1-cyclopropyl-7-[(1S,6S)-2,8-diazabicyclo[4.3.0]non-8-yl] -6,8-difluoro-1,4-dihydro-4-oxo-3-quinolinecarboxylic acid are reacted to give the title product in 42% yield.

EXAMPLE 7

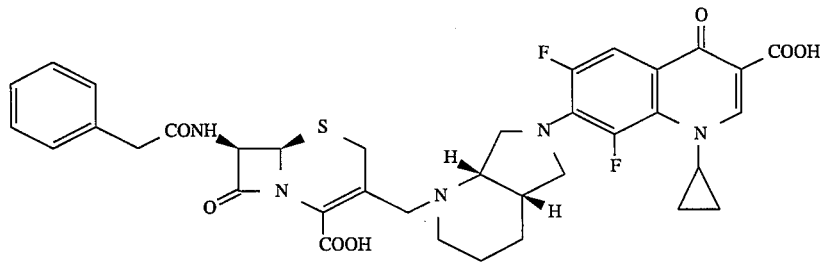

7-[2-([6R,7R]-2-Carboxy-8-oxo-7-phenyl-acetylamino- 5-thia- 1-aza-bicyclo[4.2.0]oct-2-en-3-ylmethyl)-[1S,6S]- 2,8-diazabicyclo[4.3.0]non-8-yl]-1-cyclopropyl-6,8-difluoro- 1,4-dihydro-4-oxo-3-quinolinecarboxylic acid

In the manner described in Example 2, 80 mg of the product from Example 6 were reacted to give the title compound in 40% yield.

EXAMPLE 8

7-[2-([6R,7R]-2-Carboxy-8-oxo-7-phenyl-acetylamino- 5-thia- 1-aza-bicyclo[4.2.0]oct-2-en-3-ylmethyl)-[1S,6S]-2, 8-diazabicyclo[4.3.0]non-8-yl]-8-chloro-1-cyclopropyl-6-fluoro-1,4-dihydro-4-oxo-3-quinolinecarboxylic acid disodium salt

50 ml of trifluoroacetic acid were added slowly to a solution of 9.28 g (10.28 mmol) of the benzhydryl ester from Example 1 and 10 ml of anisole in 60 ml of anhydrous dichloromethane which was stirred and cooled to 0° C. The cooling bath was removed and the reaction mixture was subsequently stirred at room temperature for a further 30 minutes. After that, 70 ml of toluene were added and the mixture was concentrated in vacuo. This process was repeated with 30 ml of toluene. The residue was decanted off and the remaining syrup was triturated with 70 ml of ether, filtered with suction, and triturated again with 100 ml of ether. This process was repeated twice. The solid thus obtained was purified in several portions using an HPLC system (column: Dynamax R-60 A, 21.4×250 mm, Rainin Instrument Company No. 83-221-C; type: C 18, particle

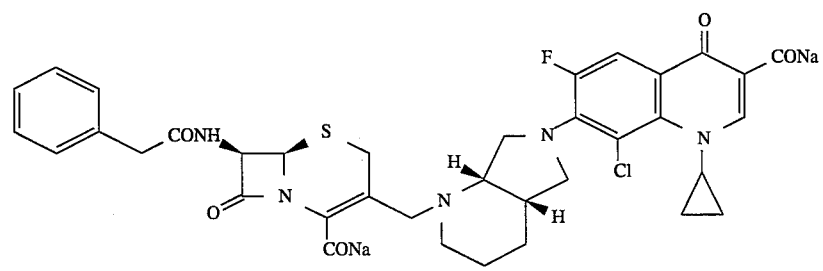

size: 8 μm; pore size 60 Å, flow rate: 30 ml/min; eluent water: acetonitrile 4:6+0.025% trifluoroacetic acid). The fractions containing the product were collected and freeze-dried. The lyophilisate was suspended in 32 ml of ice-cold water and adjusted to $pH_{8.0}$ by slowly adding 0.1N NaOH solution. The solution was filtered through a Millipore membrane (0.22 μm) and freeze-dried.

5.48 g (68%) of the title compound were obtained as a colourless lyophilisate.

$R_f$=0.27 (dichloromethane:methanol 4:1) IR(KBr) v=3434, 1750 (CO β-lactam), 1668, 1618, 1451, 1208, 1134, 802, 725 cm$^{-1}$ MS(FAB) m/z=736 (M+H)$^+$, 758 (M+Na)$^+$ 1H-NMR (300 MHz, DMSO-d$_6$) δ=0.71 (m, 2H, cyclopropyl-H), 1.15 (m, 2H, cyclopropyl-H), 1.35–1.60 (m, 4H, —CH$_2$—), 2.20 (m, 1H), 2.32 (m, 1H), 2.65 (m, 1H), 3.1–3.7 (m, 12H, SCH$_2$, PhCH$_2$CO, CH$_2$N, CHN), 3.89 (m, 1H, CH$_2$N), 4.21 (m, 1H, cyclopropyl-H), 4.92 (d, J=5 Hz, 1H, H-6'), 5.42 (dd, J=8, 5 Hz, 1H, H-7'), 7.32 (m, 5H Ph), 7.75 (d, J=15 Hz, 1H, CH=CF), 8.70 (s, 1H, NCH=C), 8.97 (d, J=8 Hz, 1H, CONH).

Decomposition point: from 138° C. $R_f$=0.22 (dichloromethane:methanol 96:4) IR(KBr) v=3420, 2937, 1738 (CO β-lactam), 1726 (CO ester), 1626, 1519, 1461, 1411, 1339, 1217, 699 cm$^{-1}$ MS(FAB) m/z=888 (M+H)$^+$ 1H-NMR (200 MHz, DMSO-d$_6$) δ=1.15 (m, 4H, cyclopropyl-H), 3.40–3.65 (m, SCH$_2$, PhCH$_2$CO, CH$_2$N, CHN, CHO), 3.9–4.1 (m, 3H, CH$_2$O, CH$_2$N, cyclopropyl-H), 5.18 (d, J=5 Hz, 1H, H-6'), 5.73 (dd, J=9.5 Hz, 1H, H-7'), 6.95 (s, 1H, CHPh$_2$), 7.2–7.5 (m, 15H, Ph) 7.24 (d, J=14H, 1H, CH=CF), 8.60 (s, 1H, NCH=C), 9.15 (d, J=8 Hz, 1H, CONH), 15.00 (s, 1H, COOH).

EXAMPLE 9

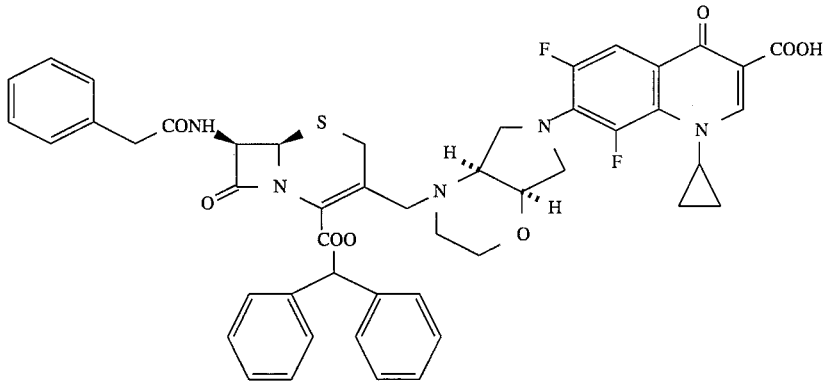

7-[2-([6R,7R]-2-Benzhydryloxycarbonyl-8-oxo-7-phenylacetylamino- 5-thia-1-aza-bicyclo[4.2.0]oct-2-en-3-yl -methyl)-[ 1R,6S]-2-oxa-5,8-diazabicyclo[4.3.0]non-8-yl]- 1-cyclopropyl- 6,8-difluoro-1,4-dihydro-4-oxo-3-quinolinecarboxylic acid As described for Example 1, 562 mg (39%) of the title compound were obtained as an amorphous powder from 876 mg (1.64 mmol) of benzhydryl [6R,7R]-3-chloromethyl-8-oxo-7-phenylacetylamino- 5-thia-1-aza-bicyclo[4.2.0]oct-2-ene-2-carboxylate and 900 mg (2.30 mmol) of the corresponding quinolonecarboxylic acid.

EXAMPLE 10

7-[2-([6R,7R]-2-Carboxy-8-oxo-7-phenyl-acetylamino-5-thia- 1-aza-bicyclo[4.2.0]oct-2-en-3-ylmethyl)-[1R,6S]-2-oxa- 5,8-diazabicyclo[4.3.0]non-8-yl]-1-cyclopropyl-6,8-difluoro- 1,4-dihydro-4-oxo-3-quinolinecarboxylic acid disodium salt As described for Example 8, 317 mg (66%) of the title compound are obtained as a colourless lyophilisate from 560 mg (0.63 mmol) of the compound from Example 9.

$R_f$=0.27 (acetonitrile:water 9:1) IR(KBr) ν=3424, 1762 (CO β-lactam), 1662, 1472, 1402, 1340, 1206, 1134, 724 cm$^{-1}$ MS(FAB) m/z=744 (M+H)$^+$ $^1$H-NMR (250 MHz, DMSO-d$_6$) δ=1.01 (m, 2H, cyclopropyl-H), 1.12 (m, 2H, cyclopropyl-H), 3.2–4.2 (m, SCH$_2$, PhCH$_2$CO, CH$_2$N, CHN, CH—O, cyclopropyl-H), 4.93 (d, J=5 Hz, 1H, H-6'), 5.42 (dd, J=5 Hz, 1H, H-7'), 7.25 (m, 5H, Ph), 7.60 (d, J=15 Hz, 1H, CH=CF), 8.52 (s, 1H, NCH=C), 9.02 (d, J=8 Hz, 1H, CONH).

We claim:

1. A compound of the formula in which

X$^1$ represents halogen,

X$^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl, R$^1$ represents alkyl having 1 to 4 carbon atoms, alkenyl having 2 to 4 carbon atoms, cycloalkyl having 3 to 6 carbon atoms, bicyclo[1.1.1]pent-1-yl, 1,1-dimethylpropargyl, 3-oxetanyl, 2-hydroxyethyl, 2-fluoroethyl, methoxy, amino, methylamino, ethylamino, dimethylamino, or phenyl which is optionally substituted by 1 or 2 fluorine atoms, R$^2$ represents hydrogen, alkyl having 1 to 5 carbon atoms, which is optionally substituted by hydroxyl, methoxy, amino, methylamino or di-methylamino, or (5-methyl-2-oxo-1,3-dioxol-4-yl)-methyl, A represents N or C—R$^5$, in which R$^5$ represents hydrogen, halogen, methyl, alkenyl having 2 to 3 carbon atoms, alkinyl having 2 to 3 carbon atoms, hydroxyl or methoxy, or can, together with R$^1$, form a bridge of the structure

—O—CH$_2$—*CH—CH$_3$, —S—CH$_2$—*CH—CH$_3$,

—CH$_2$—CH$_2$—*CH—CH$_3$ oder —O—CH$_2$—N—R$^6$, in which R$^6$ denotes hydrogen, methyl or formyl, and Z represents a residue of the structure in which D represents CH$_2$ or O, R$^3$ represents methyl or ethyl and represents the structure in which n represents 0 or 1, R$^4$ represents H, benzyl, 4-methoxybenzyl, benzhydryl, allyl, (5-methyl-2-oxo-1-dioxol-4-yl)-methyl or a radical

—CH—O—CO—R",
  |
  R' in which

R' denotes H or methyl and

R" denotes ethoxy or tert-butyl,

R$^7$ represents H or methoxy and represents H, tri-(C$_1$–C$_4$-alkyl)-silyl, acyl, C$_1$–C$_4$-alkoxycarbonyl, benzyloxycarbonyl, allyl-oxycarbonyl or isopropenyloxycarbonyl, and their pharmaceutically utilisable hydrates and acid-addition salts, as well as the alkali metal, alkaline earth metal, silver and guanidinium salts of the underlying carboxylic acids.

2. A compound according to claim 1, wherein

X$^1$ represents fluorine,

X$^2$ represents hydrogen, amino, methylamino, hydroxyl, methoxy, fluorine, chlorine, bromine or methyl, R$^1$ represents alkyl having 1 to 3 carbon atoms, vinyl, cycloalkyl having 3 to 4 carbon atoms, or phenyl which is optionally substituted by 1 or 2 fluorine atoms, R$^2$ represents hydrogen, alkyl having 1 to 2 carbon atoms, which is optionally substituted by amino, methylamino or dimethylamino, or (5-methyl-2-oxo-1,3-dioxol-4-yl)-methyl, A represents N or C—R$^5$, in which R$^5$ represents hydrogen, fluorine, chlorine, methyl, vinyl, ethinyl or methoxy, or can, together with R$^1$, form a bridge of the structure —O—CH$_2$—*CH—CH$_3$ oder —O—CH$_2$—N—CH$_3$ and Z represents a residue of the structure in which D represents CH$_2$ or O, R$^3$ represents methyl and L represents a residue of the structure

[structure: R⁸—NH—CHR⁷—CH(S)—... with β-lactam, CH₂—(O—CO)ₙ, CO—O—R⁴]

in which n represents 0 or 1,

R⁴ represents H, benzhydryl, allyl, or a radical $$-\underset{R^1}{\overset{|}{C}}H-O-CO-R^{11'}$$

in which

R¹ denotes H or methyl and

R¹¹ denotes tert-butyl,

R⁷ represents H and

R⁸ represents H, (CH₃)₃Si—, $$(CH_3)_3C-\underset{CH_3}{\overset{CH_3}{\underset{|}{\overset{|}{Si}}}}-,$$

tert-butoxycarbonyl, benzyloxycarbonyl, allyloxycarbonyl, isopropenyloxycarbonyl,

[structures: PhCH₂—CO—, thienyl-CH₂—CO—]

[structures: NC—CH₂CO—, Ph-CH(NH₂)—CO—]

[structures: NC—CH₂S—CH₂CO—, HO-C₆H₄-CH(NH₂)—CO—]

[structures: F₂CH—S—CH₂CO—, cyclohexadienyl-CH(NH₂)—CO—]

[structure: tetrazolyl-N—CH₂CO—]

[structure: Ph-CH(HN—CO—N(propyl)—C(=O)—NSO₂CH₃)—CO—]

-continued

[structure: 3,5-dichloro-4-oxo-pyridinyl—N—CH₂CO—]

[structure: HO-C₆H₄-CH(HN-CO-piperazinedione-N-C₂H₅)—CO—]

[structures: pyridyl-SCH₂—CO—, Ph-CH(OH)—CO—]

[structures: aminothiazolyl-CH₂CO (H₂N-thiazole-=CH-CH₂CO), Ph-CH(OCHO)—CO—]

[structures: Ph-CH(COOH)—CO—, Ph-CH(SO₃Na)—CO—]

[structure: aminothiazolyl-C₆H₃(NH₂)—CH—CO—]

[structure: aminothiazolyl-C(=N-OH)—CO—]

[structure: aminothiazolyl-C(=N-OCH₃)—CO—]

[structure: aminothiazolyl-C(=N-O-CONHNHCO-C₆H₃(OH)₂)—CO—]

[structure: aminothiazolyl-C(=N-O-C(CH₃)₂-CONHNHCO-C₆H₃(OH)₂)—CO—]

[structures: furyl-C(=N-OCH₃)—CO—, aminothiadiazolyl-C(=N-OCH₃)—CO—]

-continued

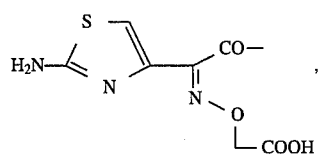

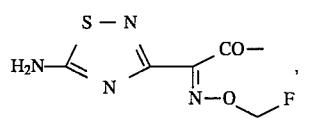

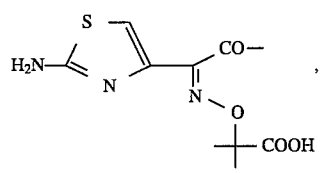

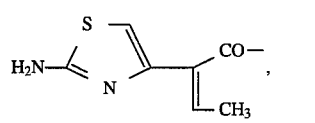

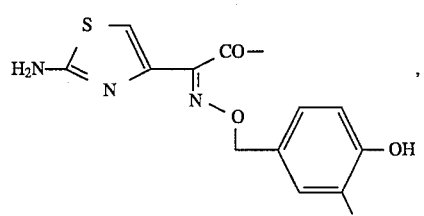

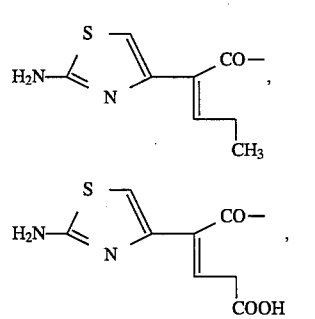

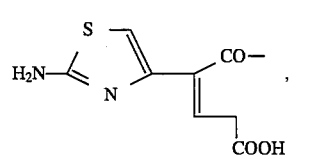

and their pharmaceutically utilisable hydrates and acid-addition salts, as well as the alkali metal, alkaline earth metal, silver and guanidinium salts of the underlying carboxylic acids.

3. A compound according to claim 1, wherein $X^1$ represents fluorine, $X^2$ represents hydrogen, amino or fluorine, $R^1$ represents alkyl having 1 to 2 carbon atoms, cyclopropyl, or phenyl which is optionally substituted by 1 or 2 fluorine atoms, $R^2$ represents hydrogen or alkyl having 1 to 2 carbon atoms, A represents N or C—$R^5$, in which $R^5$ represents hydrogen, fluorine, chlorine or methoxy, or can, together with $R^1$, form a bridge of the structure

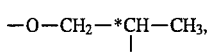

Z represents a residue of the structure

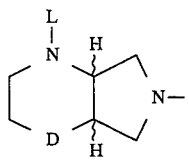

in which

D represents $CH_2$ or O,

L represents a residue of the structure

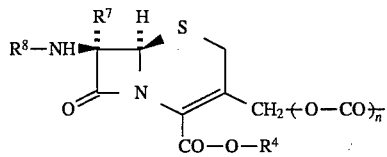

in which n represents 0 or 1, $R^4$ represents H, benzhydryl or allyl, $R^7$ represents H and $R^8$ represents H, $(CH_3)_3Si$—,

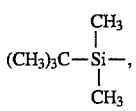

tert-butoxycarbonyl, allyloxycarbonyl,

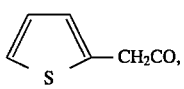

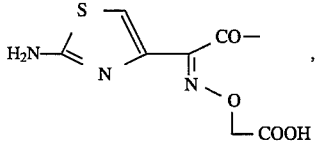

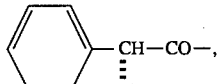

-continued

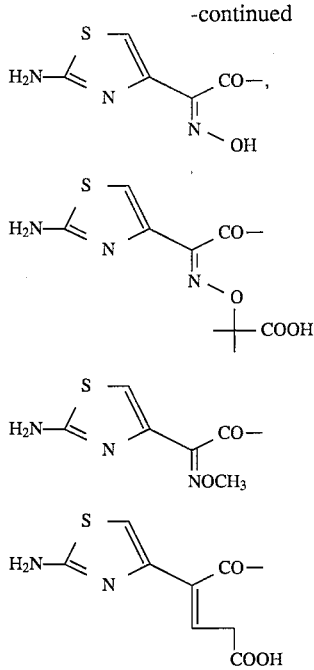

and their pharmaceutically utilisable hydrates and acid-addition salts, as well as the alkali metal, alkaline earth metal, silver and guanidinium salts the underlying carboxylic acids.

4. A pharmaceutical composition comprising a pharmaceutically effective amount of a compound or addition product thereof according to claim 1 and a diluent.

5. An antibacterial composition comprising an antibacterially effective amount of a compound or addition product thereof according to claim 1 and a diluent.

6. A composition according to claim 4 in the form of a tablet, capsule or ampule.

7. A method of combating bacteria in a patient in need thereof which comprises administering to such patient an antibacterially effective amount of a compound or addition product thereof according to claim 1.

8. A compound according to claim 1 wherein D is $CH_2$.

9. A compound according to claim 1, wherein said compound is

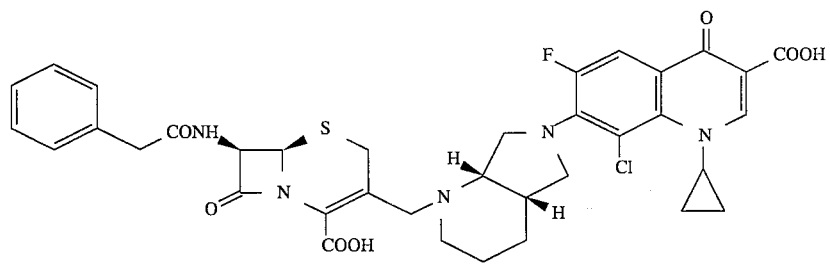

or a salt thereof.

* * * * *

UNITED STATES PATENT AND TRADEMARK OFFICE
CERTIFICATE OF CORRECTION

PATENT NO. : 5,480,879
DATED : January 2, 1996
INVENTOR(S) : Petersen, et al.

It is certified that error appears in the above-indentified patent and that said Letters Patent is hereby corrected as shown below:

Col. 74, line 1    Before " represents " insert -- L --

Col. 74, line 14   Before " dioxol " insert -- 3- --

Col. 74, line 26   Before " represents " insert -- $R^8$ --

Col. 79, line 45   After " salts " insert -- of --

Signed and Sealed this

Twenty-fifth Day of June, 1996

Attest:

BRUCE LEHMAN

*Attesting Officer*       *Commissioner of Patents and Trademarks*